United States Patent [19]
Gandolfi et al.

[11] Patent Number: 4,798,898
[45] Date of Patent: Jan. 17, 1989

[54] ANTITUSSIVE AND MUCUS REGULATING 2-SUBSTITUTED THIAZOLIDINES

[75] Inventors: Carmelo A. Gandolfi; Silvano Spinelli; Odoardo Tofanetti; Raimondo Russo; Sergio Tognella, all of Milan, Italy

[73] Assignee: Boehringer Biochemia Robin S.p.A., Milan, Italy

[21] Appl. No.: 755,834

[22] Filed: Jul. 17, 1985

[30] Foreign Application Priority Data

Jul. 27, 1984 [GB] United Kingdom ............... 8419254

[51] Int. Cl.$^4$ ............... A61K 31/425; A61K 31/38; C07C 277/04
[52] U.S. Cl. ............... 548/146; 548/152; 548/165; 548/182; 548/188; 548/200; 548/201; 514/850
[58] Field of Search ............... 548/146, 152, 165, 182, 548/188, 200, 201; 514/365, 850

[56] References Cited

U.S. PATENT DOCUMENTS

| 3,881,025 | 4/1975 | Flament | 548/146 |
| 4,011,233 | 3/1977 | Dubs et al. | 548/146 |
| 4,423,054 | 12/1983 | Iwao et al. | 548/201 |
| 4,430,344 | 2/1984 | Iwao et al. | 548/201 |
| 4,457,935 | 7/1984 | Iwao et al. | 548/201 |

Primary Examiner—Glennon H. Hollrah
Assistant Examiner—Raymond Covington
Attorney, Agent, or Firm—Armstrong, Nikaido, Marmelstein & Kubovcik

[57] ABSTRACT

2-Substituted thiazolidines compounds having formula I

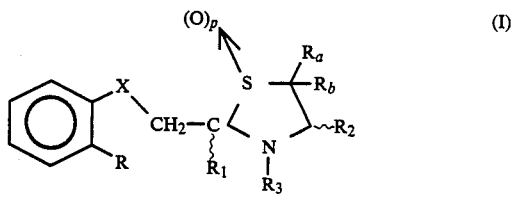

wherein X is a $CH_2$, O or S, R is hydroxy or an acyloxy, alkyloxy, alkenyloxy or alkinyloxy group, $R_1$ is hydrogen or a group of formula

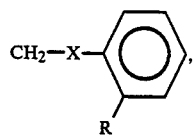

$R_2$ is hydrogen or a free or esterified carboxy group, $R_a$ and $R_b$ are hydrogen or methyl, p is zero or 1, $R_3$ is a $C_1$-$C_2$ alkylsulphonyl group, a phenyl or p-Cl phenyl, p-methylsulphonyl group or an acyl group; are useful as mucus regulating, antitussive and antibronchospastic agents.

15 Claims, No Drawings

ANTITUSSIVE AND MUCUS REGULATING 2-SUBSTITUTED THIAZOLIDINES

The present invention relates to antitussive and mucus regulating 2-substituted thiazolidines, to process for their preparation and to pharmaceutical and veterinary compositions containing them.

The compounds of the invention are 2-substituted thiazolidines of the formula (I):

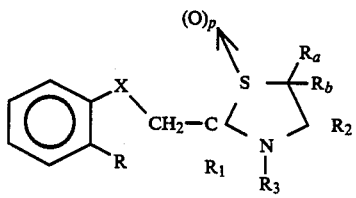

wherein:
X is a $CH_2$, O, S;
R is hydroxy, or an ester thereof of formula $R_c$—$CO_2$—, lower $C_1$-$C_6$-alkoxy, $CH_2$=CH—$CH_2O$—; HC≡C—$CH_2$—O—; methyl;
$R_1$ is hydrogen and

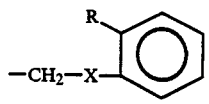

$R_2$ is hydrogen or a free or esterified carboxy group;
$R_3$ is hydrogen, a $C_1$-$C_2$ alkylsulphonyl group, an unsubstituted or mono or polysubstituted phenylsulfonyl group or an acyl group of formula $R_d$CO;
p is zero or 1 with the proviso that when X is sulfur p is zero;
both $R_a$ and $R_b$, are hydrogen or methyl; $R_c$ and $R_d$, which are the same or different are: hydrogen, O—C($CH_3$)$_3$, —($CH_2$)$_n$—Q and

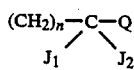

wherein n is 0 or an integer from 1 to 7; $P_1$, $J_2$, are both hydrogen or one of them is hydrogen and the other one is lower $C_1$-$C_4$ alkyl or phenyl and Q is selected in the group consisting of: hydrogen; a $C_3$-$C_4$ branched alkyl; a $C_3$-$C_7$ cycloalkyl; free or esterified carboxy group; an halogen atom; SH; —$NH_2$; a mono or di-substituted amino, t-butoxy carbonylamino or $C_1$-$C_2$ acylamino group; an ether —O—T or thioether S-T chain, wherein T is an unsubstituted or mono- or polysubstituted phenyl ring or a group of formula ($CH_2$)$_m$—$T_1$, wherein $T_1$ is selected in the group consisting of H, OH, $OCH_3$, $OC_2H_5$, $HOCH_2$—$CH_2$—, free and esterified carboxy group, $NH_2$, a $C_1$-$C_2$-acylamino or mono- or disubstituted amino group, or a group of formula

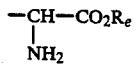

wherein $R_3$ is hydrogen, methyl or ethyl and m is an integer from 1 to 3; a phenyl, phenoxy or phenylthio ring unsubstituted or mono- or polysubstituted in the m, o, and p-positions; a group of formula —($CH_2$)$_m$—S—CO—($CH_2$)$_n$$J_3$ wherein m and n have the above defined meanings and $J_3$ is a lower $C_1$-$C_7$, linear or branched alkyl chain, a $C_3$-$C_6$-cycloalkyl, a disubstituted aminogroup, a phenyl or phenoxy ring, optionally mono- or polysubstituted in the o, m and p-positions; an alkenyl chain of formula

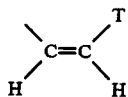

wherein T, in addition to the above defined meanings, may also be hydrogen.

The term "mono substituted amino group" comprises, within the meanings thereof, an amino group substituted by a $C_1$-$C_6$, linear or branched alkyl group or by groups having formula: —$CH_2$—$CH_2$—O—$CH_2$—$CH_3$, —$CH_2$—$CH_2$—O—$CH_2$—$CH_2$—OH, —$CH_2$—$CH_2$—NH—$CH_2$—$CH_3$, —$CH_2$—$CH_2$—NH—$CH_2$—$CH_2$—OH or

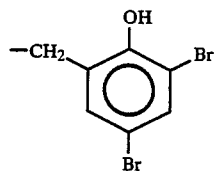

The substituents of a disubstituted amino group according to the invention may be linear or branched $C_1$-$C_6$ alkyl groups or, taken together, they represent an unsaturated or saturated nitrogen ring such as morpholin-1-yl, pyrrolidin-1yl, piperidin-1-yl, 4-methyl-piperazin-1-yl, 4-ethyl-piperazin-1-yl, 4-(2'-hydroxyethyl)piperazin-1-yl, 4-(4'-fluorophenyl)piperazin-1-yl; imidazol-1-yl, 3-pyridyl, 4-pyridyl.

Finally, the term "mono- or polysubstituted phenyl", according to the invention, means phenyl groups which are substituted by a fluorine atom in the para position, by chlorine atoms in the meta and/or para positions or by a $CF_3$ in the meta positions or phenyl group of formula

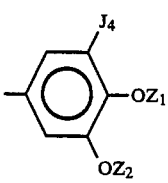

wherein $Z_1$ is H or $COCH_3$ and $Z_2$ is H, $CH_3$ or $COCH_3$ and $J_4$ is selected in the group consisting of hydrogen, aminomethyl, $C_1$-$C_2$-acylaminomethyl or mono- or di-substituted aminomethyl group, as above defined.

The optical antipodes, i.e. enantiomers, racemic mixtures thereof, diastereoisomers mixtures of compounds of formula I, have also to be considered as an object of the invention as well as non-toxic salts, both for pharmaceutical and veterinary use.

More particularly, the present invention relates to pharmaceutically acceptable base addition salts when in formula I a free carboxy group is present and to pharmaceutically acceptable acid addition salts when in formula I R₃ is hydrogen or an acyl group in which is present a basic organic moiety.

Typical examples of pharmacologically acceptable non-toxic bases are organic bases e.g. organic amines such as methylamine, dimethylamine, trimethylamine, ethylamine, diisopropylamine, N-methyl-N-hexylamine, tromethamine, cyclohexylamine, N-methyl-N-cyclohexylamine, α-phenylethylamine, β-phenylethylamine, N,N-dimethylethanolamine, N,N-diethylethanolamine, ethylenediamine, piperidine, morpholine, piperidine, piperazine, galactamine, N-methyl-glucamine, ephedrine, lysine, arginine; and inorganic bases such as alkali and alkali-earth metal hydroxydes as well as aluminium and zinc hydroxydes.

Typical examples of pharmacologically acceptable non-toxic acids are organic acids such as acetic, formic, propionic, fumaric, maleic, malic, malonic, benzoic, salicyclic, 3,4,5-trimethoxybenzoic, methanesulphonic, benzenesulphonic, canfosulphonic, lactic, aspartic, glutamic, L and D-2-phenyl-thiazolidin-5-carboxylic acid, cystin and cystein; and inorganic acids such as nitric, phosphoric, sulphoric, hydrochloric, hydrobromic acids.

Preferred salts of the invention comprise compounds of formula I wherein $R_2$ is a carboxy group salified with one of the above cited bases. Salts of piperazine and imidazole derivatives are even more preferred.

In the formulae of this specification the wavy line bond ( ) indicates that the substituent has not a definite stereochemical identity, i.e. that the substituent may be both of (R) and (S) configuration; the broken line ( ) indicates that a substituent is of (S) absolute stereochemistry; the heavy solid line ( ) indicates that a substituent is of (R) absolute configuration.

Particularly preferred compounds of the invention are those of formula I wherein $R_1$, $R_a$, $R_b$ are hydrogen, X is an oxygen atom, $R_3$ is an acyl derivative.

Compounds of formula I wherein R is alkoxy, allyloxy, propargyloxy are particularly preferred as antitussive agents.

Compounds of formula I wherein R is hydroxy and/or acyloxy are particularly preferred as mucus regulating agents.

Specific examples of preferred compounds of the invention are the following:

2-(O-methoxyphenoxy)methyl-3-acetylthioacetyl-thiazolidine;
2-(O-methoxyphenoxy)methyl-3-benzoylthioacetyl-thiazolidine;
2-(O-methoxyphenoxy)methyl-3-(3′,4′,5′-trimethoxy)-benzoylthioacetyl-thiazolidine;
2-(O-methoxyphenoxy)methyl-3-(4′-methyl-pyrazin-1-yl-acetyl-thiazolidine and its di-hydrochloride salts;
2-(O-methoxyphenoxy)methyl-3-(4′-methyl-pyrazin-1-yl)-acetyl-thioacetyl-thiazolidine and its bis hydrochloride salt;
2-(O-methoxyphenoxy)methyl-3-cyclopropylcarbonyl-thioacetyl-thiazolidine;
2-(O-methoxyphenoxy)methyl-3-(3′-cyclohexyl)propionylthioacetyl-thiazolidine;
2-(O-methoxyphenoxy)methyl-3-acetylthioacetyl-thiazolidine-sulfoxide;
2-(O-hydroxyphenoxy)methyl-3-ethoxyoxalyl-thiazolidine and its methylether;
2-(O-hydroxyphenoxy)methyl-3-cyclopropylcarbonyl-thiazolidine and its methylester;
2-(O-hydroxyphenoxy)methyl-3-imidazol-1′-yl-acetyl-thiazolidine and its methyl and ethylethers both as free base, as hydrochloride and nitrate salt;
2-(O-methoxyphenoxy)methyl-3-imidazol-1-yl-acetyl-thioacetyl-thiazolidine both as free base or as nitrate salt;
2-(O-acetylthioacetoxy-phenoxy)methyl-3-acetylthioacetyl-thiazolidine;
2-[2′-(O-acetylthioacetoxyphenyl)ethyl]-3-acetylthioacetyl-thiazolidine;
2-(O-methoxyphenylthio)methyl-3-benzoylthioacetyl-thiazolidine;
2-(O-methoxyphenylthio)methyl-3-(4′-methylpiperazin-1′-yl)acetylthioacetyl-thiazolidine;
2-(O-methoxyphenylthio)methyl-3-(4′-methylpiperazin-1′-yl)acetyl-thiazolidine both as free base and as di-hydrochloride salt;
2-[2′-(O-methoxyphenyl)ethyl]-3-benzoylthioacetyl-thiazolidine;
2-[2′-(o-methoxyphenyl)ethyl]-3-(4′-methyl-pyrazin-1-yl)acetyl-thiazolidine;
2-[2′-(O-methoxyphenyl)ethyl]-3-piperidin-1-yl-acetyl-thiazolidine;
2-(O-methoxyphenoxy)methyl-3-piperidin-1-yl-acetyl-thiazolidine;
2-(O-methoxyphenylthio)methyl-3-piperidin-1-yl-acetyl-thiazolidine;
3-(3′-morpholinomethyl-4′-hydroxy-3′-methoxy-cinnamoyl)-2-(O-methoxyphenoxy)-methyl-thiazolidine;
3-(3′-pyrrolidylmethyl-4′-hydroxy-3′-methoxy-cinnamoyl)-2-(O-hydroxyphenoxy)-methyl-thiazolidine;
3-[3-(2-hydroxyethylamino)ethylaminopropanoyl]-2-(O-methoxyphenoxy)methyl-thiazolidine and its maleate;
3-[3-(imidazol-1-yl)propionyl]-2-(O-methoxyphenoxy)-methyl-thiazolidine;
3-(3,6-dioxa-capriloyl)-2-(O-methoxyphenoxy)methyl-thiazolidine;
3-(acetylaminoacetyl)-2-(O-methoxyphenoxy)methyl-thiazolidine.

The compounds of the invention are prepared by reacting compounds of formula II

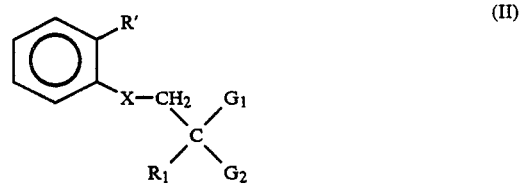

wherein
both $G_1$ and $G_2$ are a lower $C_1$–$C_2$ alkoxy or, taken together, form a carbonyl group;
R′ is a member selected from the group consisting of methyl, hydroxy, a lower $C_1$–$C_6$ alkoxy, allyloxy, propargyloxy;
X is a member selected from the group consisting of $CH_2$, S, O;
$R_1$ is hydrogen or

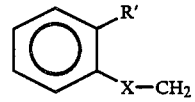

where R′ and X are as above defined, with an amino alkanethiol of formula III $$\text{HS}-\underset{\underset{\underset{R_2}{|}}{\overset{\overset{R_a}{|}}{C}}-R_b}{\overset{|}{C}}-R_b \quad \text{(III)}$$
$$\text{H}_2\text{N}-\text{C}$$

wherein $R_a$, $R_b$ and $R_2$ have the above defined meanings,
to give a compound of formula Ia (Ia)

wherein $R_a$, $R_b$, $R_2$, $R_1$, $R'$ and X are as above defined.

Compounds of formula I, wherein $R_2$ is hydrogen may be optionally subjected to optical resolution; when $R_2$ is a free and/or an esterified carboxy group, the single diastereoisomers and/or racemic mixtures of the diastereoisomers are optionally obtained.

Thiazolidines I and enantiomers or diastereoisomers thereof can be optionally subjected to subsequent acylation by reaction with an acylating agent selected in the group consisting of: tert-butoxy-carbonate, a cyclic anhydride such as succinic and glutaric anhydride or an activated species of a carboxylic acid of the formulae IVa and IVb or a sulphonyl halide of the formula IVc:

$$Q-(CH_2)_n-COZ \quad Q-\underset{\underset{J_2}{|}}{\overset{\overset{J_1}{|}}{C}}-(CH_2)_n-COZ \quad R_4-SO_2-Hal$$

IVa  IVb  IVc wherein:
Q, $J_1$, $J_2$ and n are as above defined;
$R_4$ is a $C_1$-$C_2$ alkyl group, an unsubstituted or mono or polysubstituted phenyl ring;
Hal is chlorine, bromine or iodine;
Z is a known species activating a carboxy group such as chlorine, bromine, azide, —O—CO—D where D is a $C_1$-$C_5$ lower alkoxy and benzyloxy, a $C_1$-$C_5$ lower alkyl (mixed anhydride and anhydride) and activated esters.

The obtained acyl-thiazolidines have the formula Ib (Ib)

wherein R, X, $R_a$, $R_b$, $R_1$ and $R_2$ have the above defined meanings and $R'_3$ is a group of formula $SO_2$—$R_4$ or CO—$R_d$.

The acylation reaction can also be selectively carried out only on the thiazolidine nitrogen atom; in this case R can be an hydroxy atom.

By using in the acylation reaction a carbodiimide as activating species of the carboxy group, the acylation reaction can be optionally performed by reaction of a thiazolidine of formula I with an acid of the formulae IVa, IVb wherein Z is hydroxy.

Compounds Ib wherein X is different from S, can be optionally oxidized by a suitable reagent to give compounds of formula Ic:

(Ic)

wherein the substituents have the above defined meanings.

Compounds of the general formula Id (Id)

wherein R, $R_1$, $R_2$, $R_a$, $R_b$, p are as above defined and at least one of $J_1$ or $J_2$ is hydrogen and the other is hydrogen, methyl or phenyl, Q' is an halogen atom and n is preferably zero, may be optionally reacted with a salt of a thiocarboxylic acid of the formula:

$$P_3-(CH_2)_n-CO-S^{(-)}\text{Base}^{(+)}$$

wherein $J_3$ is as above defined and the base is selected in the group consisting of sodium, potassium, magnesium, calcium, lower trialkylammonium, phenyldialkylammonium, to give the compounds of formula Id in two steps wherein Q' is $J_3$—$(CH_2)_n$—CO—S; these latter compounds can be optionally reacted with ammonia, too, to give a compounds of formula Id wherein Q' is a free thiol group from which compounds of formula Id wherein Q' is an alkylthioeter group, can be optionally obtained by reaction with an alkyl halide in the presence of a base.

Finally, the compounds of formula Id wherein n is zero, $J_1$ and $J_2$ are hydrogen and Q' is Cl, Br or I may optionally be reacted with triphenylphosphine in an inert solvent (benzene, acetonitrile, THF etc.): the obtained phosphonium salt is optionally converted into a stabilized ylide compound of the formula Ie:

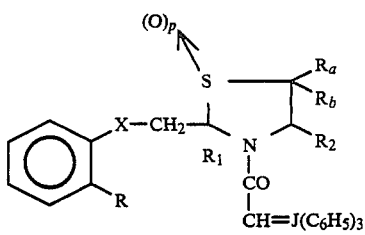

(Ie)

wherein R, $R_a$, $R_b$, $R_1$, $R_2$ and p are as above defined, with an aldehyde of the formula (V)

T—CHO  (V)

wherein T is also as above defined, to give, after optional removal of the protective groups, 3-thiazolidine acrylamides of the formula If

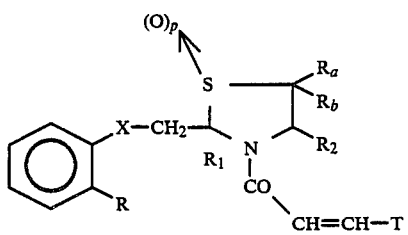

(If)

which, when T is H, $C_1$-$C_4$-lower alkyl and phenyl, can be optionally reacted with nucleophiles such as amines (i.e. $H_2N$—$(CH_2)_m$—$T_1$, monosubstituted and disubstituted amines) and thiols (i.e.: HS—$(CH_2)_m$—$T_1$, unsubstituted or mono or polysubstituted thiophenols) to obtain a Michael adduct of formula (Ig)

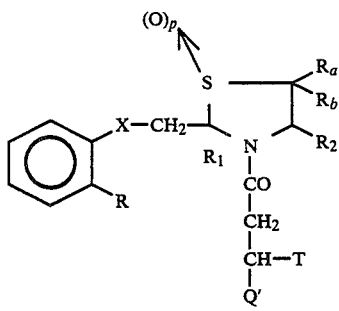

(Ig)

wherein R, $R_1$, $R_a$, $R_b$, $R_2$, p, x are as above defined and Q' is selected in the group consisting of HN—$(CH_2)_m$—$T_1$, mono and disubstituted amino group, S—$(CH_2)_n$—$T_1$ (m, n and $T_1$ are as above defined) unsubstituted, mono or polysubstituted phenylthio group and n is 1.

When in the above general formulae Ib-Id R represents an esterified hydroxy group ($R_cCO_2$—), the protective ester group can be selectively removed and the resulting hydroxy group may be optionally subjected to selective esterification.

The cyclization of a compound of formula II with an aminealkanethiol of formula III to form a 2-substituted thiazolidine ring may be performed by reaction with either a stoichiometric amount or a small excess of the amine alkanethiol in an aqueous solvent, either in the presence or absence of a catalytic amount of its ammonium salt such as acetate, formiate, canfosufonate, hydrochloride.

Suitable solvents are, for example, water, methanol, ethanol, acetic acid and mixtures thereof.

The reaction is preferably carried out at temperatures ranging from about −20° C. to the solvent's reflux temperature; preferably the reaction is performed at room temperature.

The reaction times range from few minutes to several days, but usually they do not exceed two hours and often a few minutes are sufficient to complete the reaction.

The optical resolution of the compounds of formula Ia may be optionally carried out by salification with an optically active acid such as for example d- and l-canfosulphonic acid, d- and l-lactic acid, d- and l-mandelic acid, d- and l-6-exo-chloro-7-syncarboxy-bicyclo[2,2,1]-heptan-3-one-3,3-ethylendioxy followed by crystallization till constant rotatory power and recovery of the optically active 2-substituted-thiazolidine.

Suitable solvents are, for example, alcohols such as methanol, ethanol, 1-propanol, 2-propanol, ethers such as ethylether, isopropylether, dioxane, tetrahydrofuran, esters such as ethylformiate and ethylacetate and hydrocarbons such as benzene, toluene, cyclohexane, hexane and mixtures thereof.

The optical resolution is preferably carried out at room temperature and few crystallizations are generally necessary to obtain a constant rotatory power.

The optional acylation of the compounds of formula Ia with an acylating agent of formula IV may be performed by reaction with either a stoichiometric amount or a small excess of acylating agent in an inert solvent in the presence of either a stoichiometric amount or of an excess of a base. Suitable solvents are, for example, halogenated hydrocarbons such as $CH_2Cl_2$, $CHCl_3$, Cl—$CH_2CH_2Cl$; ketones such as acetone and butan-2-one; hydrocarbons such as hexane, cyclohexane, benzene, toluene, pyridine and mixtures thereof.

A nearly stoichiometric amount of base for any molecule of the acylating agent is useful. Such a base may be an inorganic base e.g. an alkali or an alkali-earth metal oxide, carbonate or bicarbonate, e.g. CaO, $CaCO_3$, $K_2CO_3$, $KHCO_3$, $Na_2CO_3$, $NaHCO_3$; an organic base such as a tertiary amine, e.g. trimethylamine, tributylamine; or an aromatic base, e.g. pyridine, an alkyl substituted pyridine, a N,N-dialkyl-aniline; or an anionic ion-exchange resin.

The acylation reaction is preferably carried out at room temperatures ranging from about −40° to about the solvent's reflux temperature, preferably the reaction is performed at room temperature.

A temperature below 0° C., ranging from −40° to about −50° may be preferably used when a free phenolic group is also present and an equivalent of the acylating agent is used in order to obtain the optional acylation of the thiazolidine ring without affecting the phenolic group.

Using in the acylation reaction, a carboxylic acid of formula IVa and IVb (Z=OH), the reaction is performed in the presence of an excess of a condensating agent, such as a carbodiimide and preferably dicyclohexylcarbodiimide, in an inert solvent, at room temperature, in the presence or absence of catalytic amounts of 4-dimethylaminopyridine.

The optional oxidation of the compounds of formula Ib to obtain a thiazolidine sulphoxide of formula Ic may be performed by reaction with either a stoichiometric amount or a small excess of an organic peracid such as monoperphtalic acid, m-chloroperbenzoic acid, peracetic acid, performic acid and perbenzoic acid in an inert solvent either in the presence or in the absence of a base.

Preferred oxidizing agent is a stoichiometric amount of monoperphtalic acid, the preferred solvent is ethyl acetate and the reaction is preferably performed in the presence of an excess of $NaHCO_3$.

The oxidation reaction is preferably carried out at temperature ranging from about $-25°$ C. to room temperature; preferably the reaction is performed at $0°$ C.

The thiolation of a compound of formula Id wherein Q' is a halogen atom may be optionally performed by treatment with either a stoichiometric amount or an excess of a salt of a thiocarboxylic acid and/or of thiophenol acid such as for example, sodium, potassium salt and/or "in situ" formed salt of the thiocarboxylic acid with a generic organic base such as trimethylamine, triethylamine, tributylamine, in an inert solvent.

Suitable solvents are, for example, halogenated hydrocarbons, ketones, esters, ethers, alcohols and the mixtures thereof.

The reaction is preferably carried out at room temperature and the reaction times range from few minutes to several hours but, usually, the reaction times do not exceed two hours at room temperature.

A free thiol group may be optionally obtained reacting the thioacyl compounds with an excess of aqueous ammonia solution in inert gas atmosphere at room temperature.

The reaction is optionally performed at room temperature, suitable solvents are alcohols such as methanol, ethanol, glycols and ethers miscible with aqueous ammonia solutions such as dimethoxyethane, dioxane, tetrahydrofurane and mixtures thereof.

The optional acylation of the free thiol and phenolic group may be performed as above described.

The optional alkylation of the free thiol group may be performed by treatment of the potassium and/or sodium salt of the thiol compound with an alkyl halide.

The reaction between the stabilized ylides of the formula Ie and the aldehydes of formula V is the well-known Witting reaction whose experimental procedure is also well-known; it is generally performed by mixing the reagents in equimolecular ratio in an inert solvent such as an halogenated solvent, an ethereal solvent (THF, dimethoxyethane, etc.), hydrocarbons (cyclohexane, benzene, toluene, hexane), acetonitrile or using a mixture thereof, preferably at room temperature.

The Michael addition of the above defined nucleophiles to the acrylamides of the formula Ia is also a well-known reaction. Preferred solvents are alcohols and the reaction is carried out by mixing the reagent and heating at the reflux temperature.

The thiazolidines of formula I wherein R is hydroxy and $R_3$ is $-CO_2C(CH_3)_3$ may be optionally reacted with a lower $C_1-C_6$-alkyl halide, a propargyl halide and allylhalide in an aprotic solvent such as dimethylformamide in the presence of potassium carbonate to give a compound of formula I wherein R is a lower $C_1-C_6$ alkoxy, $CH_2=CH-CH_2-O-$ and $HC\equiv CH-CH_2O$.

The subsequent optional cleavage with trifluoroacetic acid of the protective tert-butoxy-carbonyl group affords the corresponding thiazolidines of formula I, wherein R is a lower $C_1-C_6$ alkoxy, allyloxy and propargyloxy and $R_1$ is hydrogen.

The compounds of formula II are known compounds or may be prepared by known methods.

Particularly 2-ξ-hydroxy-3,4-dihydroxy-benzopyrane, and 2-ξ-hydroxy-1,4-benzodiaxane are optionally prepared by reduction with DIBAH of the corresponding lactones i.e. 3,4-dihydro-benzopyran-2-one (dihydrocoumarin) and 1,4-benzodioxan-2-one.

Also the amine alkanethiol of formula III, the acylating agents of formula IV and the thiocarboxylic acids and the aldehydes of formula V are known compounds or may be prepared by known methods.

The compounds of the invention are therapeutically active substances, devoid of acute, subacute or chronic toxic effects, suitable for use as antitussive agents and mucus regulating agents.

In fact for example the compounds of the invention never exhibit acute toxic effects in mice and rats.

$LD_{50}$ values above 1 g/kg are generally determined both after oral and intraperitoneal administration of the compounds of the invention.

The compound 4-carboethoxy-3-acetylthioacetyl-2-(o-methoxyphenoxy)methyl-thiazolidine differs from the other ones, because it shows in mice $LD_{50}$ such as 0,76 g/kg (os) and 0.67 g/kg (i.p.). A sedative effect, starting from 30 mg/kg, is also present.

The techniques described by Charlier et al. (Arch. Int. Pharmacodyn. 134, 306, 1961) and by Stefko et al. (J. Pharm. Exp. Therap., 108, 217, 1953), adapted with minor modifications, are used to investigate the antitussive properties of the compounds of the invention. Codeine phosphate is used as positive reference compound.

According to the Charlier procedure guinea pigs are exposed to a citric acid aerosol (7.5%) and cough is recorded 60 minutes after the antitussive treatment by i.p. route. Male animals of 300–400 g pigs are placed in perspex box ($20 \times 30 \times 30$ cm) connected to an aerosol compressor; the animals are subjected to a citric acid saturated atmosphere, 60 minutes after the i.p. injection of a compound of the invention (0.1 and 0.3M solutions; 1 ml/kg).

The total number of cough strokes and the delay of the first cough are recorded during the first five minutes.

Five guinea pigs are used for each dose level and the results are compared with controls (vehicle treatment) and codeine phosphate 0.07M solution (standard treatment).

$ED_{50}$ and the corresponding delay of first cough stroke are calculated.

The data obtained by i.p. administration are confirmed by oral administration.

In the Stefko procedure, conscious mongrel dogs ($15 \pm 3$ kg body weight) are used; the compounds of the invention are tested for their ability to inhibit cough induced by electric stimulation.

Under general anesthesia, two insulated nichrome wires (0.4 mm diameter) are surgically implanted into the submucosa of the trachea.

About two days later, the dogs are placed in a sling and the exteriorized electrodes are connected to an electric stimulating device (such as Grass S 48 Mod.).

The stimulation parameters such as: delay 0.01 msec, duration 1 msec, frequency 30 Hz, are used.

An electrical stimulus of 1 sec is applied 10 times at 5 sec intervals in order to determine the minimum voltage necessary for eliciting reproducible cough responses. Then, tussive responses to the electrical stimuli are registered at 15, 30, 60, 90, 120, 150, 180, 240, 300 and 360 minutes after oral administration of the compounds of the invention.

The tussive responses are scored as follows: 1: no response; 2: sigh or exaggerated expiration; 3: marked cough; 4: one marked cough and one exaggerated expiration: 5: two marked coughs.

Six dogs are employed for each determination and the mean activity is calculated.

The inhibition percent of the cough response and the duration of activity are compared with codeine.

In the guinea pig cough test, codeine phosphate shows an $ED_{50} \simeq 23$ mg/kg with a 170% delay.

In the dog cough test, codeine phosphate when tested at 8 mg/kg shows a 52% inhibition of the cough stimulus for a long time (about 2-4 hours).

The mucus regulating properties of the compounds of the invention are investigated "in vivo" by means of experiments carried out on male New Zealand white rabbits. The animals are submitted to inhalation of a 5% $H_2SO_3$ aqueous solution by aerosol (exposition of 3 hours a day for 3 alternate days), to induce a chronic bronchial inflammatory disease which causes a production of pathological sputum in the bronchial tree.

Aim of the experiments is to evaluate modifications of selective parameters such as dry weight of the sputum, viscosity, content in proteins, phospholipids, galactose, sialic acid and fucose, induced in this pathological sputum by pharmacological treatment with the compounds of the invention.

To this purpose, the sputum produced in the bronchial tree is collected daily, through a "T" shaped glass cannula, inserted in the trachea, before and after oral twice a day (9.00 a.m. and 4.00 p.m.) treatment with one of the compounds of the invention.

The schedule treatment procedure is shown in the following Scheme 1:

Scheme 1

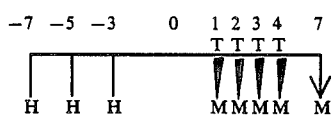

where 0 indicates the day of implantation of the tracheal cannula; -7-5-3 indicate the days of $H_2SO_3$ treatment (H); 1, 2, 3, 4 indicate the days of oral administration of the compounds of the invention (T) and the time of mucus collection (M).

The mucus collected in day 1 in the morning is considered as a blank; 7 indicates the day of the animal sacrifice after the mucous collection.

The sputum samples are stored in the freezer ($-20°$ C.) until the investigation of biological and rheological parameters is carried out.

The samples are investigated for relative viscosity, measured at 37° C. with a Brookfield viscometer (model LT VD) equipped with a 1,565° cone-plate, and aliquoted for biochemical analysis of protein, phospholipids, galactose, sialic acid and fucose contents. Dry weight of the mucus is also determined. For each parameter, cumulative data are referred to a seven days period after the beginning of the treatment and they are extrapolated using the AUC method (area under curve) calculated by the trapazoidal rule. Finally the data are compared with data obtained from controls (vehicle treatment), non bronchitic rabbits (vehicle treatment) and positive controls bronchitic rabbits treated with 0.153M 2-carboxymethyl cysteine.

In Table 1 the AUC values, determined for the various parameters, after the treatment of bronchitic rabbits with S-carboxymethyl cysteine are reported.

TABLE 1

| | AUC as a % compared to bronchitic controls | | | | | | |
|---|---|---|---|---|---|---|---|
| Treatment | Viscosity (cps) | Mucus production ml/kg | Protein mg/ml | Phospholipids mg/ml | Galactose mg/ml | Sialic acid mg/ml | Fucose mg/ml |
| Controls | 100 | 100 | 100 | 100 | 100 | 100 | 100 |
| S—carboxymethyl cysteine 0.153 M | 52 | 97 | 105 | 108 | 64 | 60 | 56 |

As it is evident, all the parameters are influenced by the pharmacological treatment with S-carboxymethyl cysteine.

An ideal mucoregulating agent should reduce the viscosity and the protein content of the mucus.

In pathological cases, the high protein content of the mucus could be related to an abnormal production of the mucus macromolecules and also to an abnormal passive transport of seric proteins through the capillary vessels.

At the same time, the reduction of the mucoprotein content should be associated with a reduction of the contents of galactose and sialic acid in the sputum, so indicating a lower tendency to produce mucines which contribute to the viscosity of the mucus.

Fucose content is related to the production of neutral mucines.

The increase in the mucus volume is connected to a reparative local process for which a liquefaction of the mucus is obtained. This event is particularly desirable when, as in some pathological conditions, the mucus of the patients appears to be adhesive and highly viscous, so contributing to the obstruction of the respiratory ways.

The results obtained with some compounds of the invention, administered orally in equimolecular amounts in comparison with the standard S-carboxymethyl cysteine, are shown in Table 2.

TABLE 2

| Treatment | AUC as a 100% compared to bronchitic controls | | | | | | |
|---|---|---|---|---|---|---|---|
| | Viscosity (cps) | Mucus production (ml/kg) | Protein (mg/ml) | Phospholipids (mg/ml) | Galactose (mg/ml) | Sialic acid (mg/ml) | Fucose (mg/ml) |
| animal untreated with H$_2$SO$_3$ | 90 | 72 | 96 | 79 | 30 | 78 | 85 |
| bronchitic animal (5% H$_2$SO$_3$ aerosol) | 100 | 100 | 100 | 100 | 100 | 100 | 100 |
| 2-(o-methoxyphenoxy)-methyl-thiazolidine | 116 | 124 | 92 | 106 | 59 | 85 | 76 |
| 2-(o-methoxyphenoxy)-methyl-thiazolidine-4-carboxy | 40 | 95 | 48 | 49 | 29 | 52 | 55 |
| 2-(o-methoxyphenoxy)-methyl-thiazolidine-3-acetyl-thioacetyl | 59 | 127 | 78 | 37 | 57 | 107 | 151 |
| 2-(o-methoxyphenoxy)-methyl-thiazolidine-3-acetylthioacetyl-4-carbethoxy | 91 | 65 | 79 | 102 | 69 | 78 | 111 |
| 2-(o-methoxyphenoxy)-methyl-3-(ethoxyoxalyl)-thiazolidine | 65.1 | 108.7 | 62 | 59.8 | 52.3 | 56.8 | 149.3 |
| 2-(o-methoxyphenoxy)-methyl-3-cyclopropyl-carbonyl-thiazolidine | 92.6 | 90 | 57.9 | 74.5 | 60.0 | 60 | 103.6 |
| 2-(o-acetylthioacetoxyphenoxy)methyl-3-acetylthioacetyl-thiazolidine | 71.9 | 74.0 | 46.9 | 49.8 | 72.9 | 31.3 | 147.9 |
| 2-(o-methoxyphenoxy)-methyl-3-(2'-imidazol-1'''-yl)acetyl-thiazolidine | 39.1 | 162.5 | 55.2 | 65.8 | 21.8 | 63.8 | 97.5 |
| 2-(o-hydroxyphenoxy)-methyl-3-acetylthioacetyl-thiazolidine | 31.9 | 99.2 | 62.0 | 47 | 38.2 | 49.5 | 90.8 |
| 2-[2'-(o-acetylthioacetoxyphenoxy)methyl]-3-acetylthioacetyl-thiazolidine | 70 | 76.1 | 48 | 47.2 | 67 | 36.2 | 128 |

3-Acetylthioacetyl-2-(o-methoxyphenoxymethyl)-thiazolidine is a typical compound of the invention having mucus regulating properties as well as good antitussive activity.

The compound shows an ED$_{50}$ lower than 5 mg/kg (185% delay) in the guinea pig cough test. At doses of 20 mg/kg, this acetylthiothiazolidine compound shows a 54.2% inhibition of the cough stimulus in the dog also exhibiting a more favourable duration of action in comparison to codeine.

Other compounds of the invention such as: 3-benzoylthioacetyl-2-(o-methoxyphenoxy)methylthiazolidine; 3-(3'-cyclohexyl)propionylthioacetyl-2-(o-methoxyphenoxy)methylthiazolidine; 3-(4'-methyl-piperazin-1'-yl)acetylthioacetyl-2-(o-methoxyphenoxy)-methyl thiazolidine.2HCl; 3-(4'-methylpiperazin-1'-yl)acetyl-2-(o-methoxyphenoxy)methylthiazolidine.2HCl; 3-acetylthioacetyl-2-(o-methoxyphenylthio)methyl-thiazolidine, and 3-acetylthioacetyl-2-[2'-(o-methoxyphenyl)ethyl]-methyl-thiazolidine exhibit in the guinea pig cough test ED$_{50}$ ranging from 0.5 to 4 mg/kg with a % delay of the first cough (control 100) also ranging from 135 to 316%.

The guinea pig cough test and the dog cough test are effective and reliable testing procedures for the screening of substances useful in the treatment of cough of different origines and in the relief of the pain induced by tussive attacks.

Accordingly, the compounds of the invention may be useful in the treatment of patients in order to reduce and to prevent tussive attacks. Therefore the compounds of the invention are also useful to stop paroxysm of coughing which could precipitate syncope.

Prevention and stopping strenuous coughing is also highly useful because cough may produce rupture of an emphysematous bled and rib fractures.

Although cough fractures of the ribs may occur in otherwise normal patients, their occurrence should at least raise the possibility of pathologic fractures, which are seen in multiple myeloma, osteoporosis and osteolytic metastase.

Particularly preferred compounds of the invention as antitussive agents are compounds like 3-(acylthioacetyl)-2-(o-methoxyphenoxy)methylthiazolidine and/or 3-(methylpiperazinacetyl)-2-(o-methoxyphenoxy)-methylthiazolidine and/or 3-(methylpiperazinoacetyl-thioacetyl)-2-(o-methoxyphenoxy)methylthiazolidine.

Further preferred compounds are their 2-(o-methoxyphenylthio)methyl- and their 2-[2'-(o-methoxyphenyl)ethyl]-analogues which are endowed with a strong antitussive property together with a comparatively faible mucus regulator activity.

A decrease of the antitussive potency together with a favourable increase of the mucus regulating ability is surprisingly noted, when in compounds 1 the alkoxy, allyloxy and propargyloxy groups of R are substituted by a hydroxy or an acyloxy group, as it can be noticed, for example, from the data reported in Table 2, particularly for the compounds 3, 9, 7, 10.

In the guinea pig cough test, the compounds 9, 7, 10 exhibit ED$_{50}$ such as 60, 162 and 61 mg/kg, respectively, indicating an almost 10 times decrease of the antitussive potency in comparison with the reference compound 3 ($ED_{50}\simeq 5$ mg/kg). To this decrease of potency as antitussive agents corresponds a particularly favourable increase of their mucus regulating activity.

These latter data provide also evidence that a changing in X, i.e. a methylene group instead of oxygen, increases the antitussive potency.

In Table 3 some data reported relating to the antitussive properties of some 4-carboxy-thiazolidines of the invention.

TABLE 3

| Compound | Guinea pig cough test $ED_{50}$ (mg/kg) | Guinea pig cough test % delay | Dog cough test % inhibition of cough stimulus | Dog cough test duration of action |
|---|---|---|---|---|
| 2-(o-methoxyphenoxy)methyl-4-carboxythiazolidine | inactive | — | 43.8 | middle |
| 2-(o-methoxyphenoxy)methyl-4-carbethoxythiazolidine | inactive | — | 26.7 | short |
| 2-(o-methoxyphenoxy)methyl-3-acetylthioacetylthiazolidine | 77.1 | 350 | — | — |

On the other hand, compounds such as 3-(ethoxyoxalyl)- and 3-(cyclopropyl)carboxyl-2-(o-methoxyphenoxy)methylthiazolidine appear to be devoid of any antitussive properties both in the guinea pig and dog cough tests. 3-(Imidazol-1'-yl)acetyl-2-(o-methoxyphenoxy)methylthiazolidine and its 2-(o-hydroxyphenoxy)methyl-analogue display a reduced antitussive potency ($ED_{50}$ 40.6 mg/kg and 96 mg/kg respectively, while retaining a strong mucus regulating activity (see table 1)).

This graduality in antitussive potency together with a very high mucus regulating activity is highly desirable in some pathological conditions such as chronic bronchitis, in which it is not always desirable to suppress a cough productive of significant quantities of sputum. In some cases, an early suppression of the cough could mean ritention of the mucus in the tracheobronchial tree, negative interference with the distribution of the ventilation alveolar aeration and with the ability of the lung to resist infections.

The changes induced in the mucus by the treatment with selective mucus regulators as a consequence may reduce the number of cough attacks.

In accordance with this aim particularly useful and preferred substances which exhibit a high mucus regulating activity together with a reduced antitussive potency are 2-(o-hydroxyphenoxy)methyl-4-carboxythiazolidine, 2-(hydroxyphenoxy)methyl-thiazolidines 3-substituted with 3-alkoxyoxalyl, 3-cyclopropylcarbonyl-, 3-(imidazol-1-yl)acetyl, 3-(3',4'-dihydroxy)cinnamoyl, 3-(3'-methoxy-4'-hydroxy)cinnamoyl groups.

Bis-2-(o-methoxyphenoxy)methyl-thiazolidines such as the 3-acetylthioacetyl and the 4-carboethoxy derivatives show also antitussive properties with $ED_{50}$ values of 230 and 116 mg/kg respectively. The 3-acetylthio compound is also active in the dog cough test (13% inhibition of the cough stimulus) in which it shows a very prolonged action (2–3 times longer than that of codeine phosphate).

In contrast to the 2-(o-methoxyphenoxy)methyl-3-acetylthioacetylthiazolidine, its 2-(o-tolyloxy)methyl analogue is devoid of any antitussive properties. In addition, when tested as mucus regulator, it increases viscosity, protein and fucose content in the mucus, poorly affecting galactose and sialic content. Also 2-tolyloxy-methyl-3-(imidazol-1'-yl)acetylthiazolidine is not active in the cough tests, exhibiting some mucus regulating action in the bronchitic rabbits, with a spectrum of action very close to that of carboxymethylcysteine.

Some compounds of the invention display also a protecting action on the liver of mice against paracetamol and $CCl_4$ poisoning.

The compounds 3-[(3,6-dioxa-capriloyl)-2-(O-methoxyphenoxy)-methyl-thiazolidine, 3-(3-thia-6-oxacapriloyl)-2-(O-methoxyphenoxy)-methyl-thiazolidine, 3-(3-imidazolyl-propionyl)-2-(O-methoxyphenoxy)-methyl-thiazolidine, 3-(3'-imidazol-1-yl)-propionyl-2-(O-propargyloxyphenoxymethyl)-thiazolidine, when tested to a dosage level 0.01–0.08M, are mucus regulating agents at least as effective as 0.153M of 5-carboxymethylcysteine.

Moreover, the compounds 3-(acetylglicinyl)-2-(O-methoxyphenoxy)-methyl-thiazolidine, 3-BOC-2-(O-methoxyphenoxy)-methyl-thiazolidine, 3-glicinyl-2-(O-methoxyphenoxy)-methyl-thiazolidine and its 2-(O-allyloxyphenoxy)-methyl analogue are also endowed with good antitussive properties with $ED_{50}$ ranging from 3 to 30 mg/kg.

The compounds 3-[3-(2-(2-hydroxyethylamino)ethylamino)propionyl)]-2-(O-methoxyphenoxy)-methyl-thiazolidine maleate and its 2-O-propargyloxy analogue are also particularly effective as antitussive agents with an $ED_{50}$ ranging from 3 to 6 mg/kg and are both characterized by a very prolonged duration of action.

The compounds of the invention are also characterized by a pronounced ability to induce relaxation of the bronchial and tracheal smooth muscle.

For instance, 3-(3'-morpholinomethyl-4'-hydroxy-5'-methoxy-cinnamoyl)-2-(O-methoxyphenoxy)-methyl-thiazolidine.HCl is able to relaxe "in vitro" guinea pig trachea smooth muscle strips contracted by methacoline with $ED_{50}$ of $1.9 \times 10^{-4}$M. The spasmolytic activity of the new substance favourably compares with that of dihydroxypropyltheophylline ($ED_{50}$ $0.76 \times 10^{-4}$M). After intrajugular administration, the compound appears 3–6 times more active than aminophylline in the resolution of bronchospasm induced by i.v. histamine in anesthethized guinea-pigs (Konzett-Ressler test).

Therefore, compounds I are effective antitussive, bonchodilating and mucus regulating agents. They may be administered by oral, sublingual, intravenous, subcutaneous, intramuscular, rectal or inhalatory route.

The inhalatory route is particularly preferred when a muscus regulating action is requested.

The preferred doses of the compounds range from 0.05 to about 5 mg/kg/day, according to the patient's conditions, weight, age, and administration route.

The preferred doses by inhalatory route range from 0.05 to 1 mg/kg/day.

As previously stated, the compounds of the invention can be administered either to humans or animals in a variety of dosage forms, e.g., orally in the form of tablets, capsules, or liquids; rectally, in the form of suppositories; parenterally, subcutaneously of intramuscularly, with intravenous administration being preferred in emergency situations; by inhalation in the form of aerosols or solutions for nebulizers; in the form of sterile implants for prolonged action. The pharmaceutical or veterinary compositions containing the compounds of the invention may be prepared in conventional ways and contain conventional carriers and/or diluents.

For example, for intravenous injection or infusion, sterile aqueous isotonic solutions are preferred. For subcutaneous or intramuscular injection, sterile solutions or suspensions in aqueous or non-aqueous media may be used; for tissue implants, a sterile tablet or silicone rubber capsule, containing or impregnated with the compound, is used.

Conventional carriers or diluents are, for example, water, gelatine, lactose, dextrose, saccharose, mannitol, sorbitol, cellulose, talc, stearic acid, calcium or magnesium stearate, glycol, starch, arabic gum, tragacanth gum, alginic acid or alginates, lecithin, polysorbate, vegetable oils, etc.

For administration by nebulizer, a suspension or a solution of the compound of the invention, preferably in the form of a salt, such as the sodium salt in water (and-/or the nitrate salt) can be used. Alternatively, the pharmaceutical preparation can be in the form of a suspension or of a solution of the compound of the invention in one of the usual liquefied propellants, such as dichlorodifluoromethane or dichlorotetrafluoroethane, administered from a pressurized container such as an aerosol bomb. When the compound is not soluble in the propellant it may be necessary to add a co-solvent, such as ethanol, dipropylene glycol and/or a surfactant to the pharmaceutical formulation.

The following examples illustrate but do not limit the present invention.

EXAMPLE 1

A solution of potassium hydroxyde (8.46 g) in 2-propanol and water (3 ml) is added to a mixture of pyrocathechine monomethyl ether (28.5 g) and epichlorohydrin (10 ml) in 2-propanol (320 ml). The mixture is heated to reflux for 2 hours, the excess of the solvent is distilled out and the residue is poured in ice-water. The precipitate is filtered and crystallized from isopropylether to give 1,3-di-o-methoxyphenoxypropan-2-ol (28.8 g); m.p. 73°–75°.

A solution of this compound in dry benzene-DMSO (3:1, 250 ml) is treated with dicyclohexylcarbodiimide (55 g), pyridine (8 ml) and trifluoroacetic acid (4 ml). The mixture is stirred for 3 hours at room temperature, then the excess of reagent is destroyed by cautious addition of a solution of oxalic acid (10 g) in methanol (20 ml). The mixture is diluted with water (150 ml) and filtered to remove the precipitated dicyclohexylurea. The organic phase is separated, washed with water, dried on $Na_2SO_4$ and the solvents are evaporated in vacuum. The residue oil is crystallized from $Et_2O$ to yield 1,3-di-o-methoxyphenoxy-propan-2-one (22 g) m.p. 64°–66° C.

Cysteamine acetate, obtained from cysteamine(2-amine-ethanethiol)hydrochloride (3.6 g) and sodium acetate (4.52 g) is added to a solution of 1,3-di-o-methoxyphenoxy-propan-2-one (8 g) in ethanol (60 ml). The mixture is stirred for 3 days at room temperature, the ethanol is evaporated off and the residue is partitioned between water and $CH_2Cl_2$. The organic phases are collected, washed with water, dried on $MgSO_4$. After evaporation of the solvents under vacuum, the oil is crystallized from $Et_2O$ to give 7.8 g of 2,2-di(o-methoxyphenoxy)methyl-thiazolidine m.p. 86°–88° C. ($R_f$=0.5 on $SiO_2$ $CH_2Cl_2$/EtOAc 4:1). An analytical sample from ethanol shows m.p. 91°–93° C.

EXAMPLE 2

Following the procedure described in Example 1 but using L-cysteine hydrochloride, 2,2-di(o-methoxyphenoxy)methyl-4-carboxy-thiazolidine m.p. 160°–162° C. is obtained.

EXAMPLE 3

Following the procedure described in Example 1, but using L-cysteine ethyl ester hydrochloride, 2,2-di(o-methoxyphenoxy)methyl-4-carbethoxythiazolidine (EtOH), is obtained, as an oil, $[\alpha]_D$ −53°; $[\alpha]_{365}$=−138°.

EXAMPLE 4

Under an inert gas athmosphere a 1M DIBAH (diisobutylaluminum hydride) solution in toluene (150 ml) is added dropwise to a stirred solution of 3,4-dihydrobenzopyran-2-one (20 g) in dry toluene (200 ml) cooled at −70° C., in 20 minutes.

Stirring is continued for additional 20 minutes, then the excess reagent is destroyed by adding a 2M isopropanol solution in toluene (50 ml). The mixture is warmed at room temperature and treated with water (5 ml) and anhydrous $Na_2SO_4$ (40 g) under continous stirring. The inorganic material is filtered off and the organic eluate is evaporated to dryness under vacuum to give crude 3,4-dihydro-2-hydroxy-benzopyrane (19.4 g).

A solution of this compound in EtOH (70 ml) is treated with an aqueous solution of cysteamine acetate prepared by mixing cysteamine hydrochloride (18 g) and potassium acetate (16.2 g) in water (30 ml).

The reaction mixture is stirred for 30 minutes at room temperature and diluted with water (200 ml). The precipitate is filtered and after drying in vacuum is crystallized from isopropylether to give 2-[2'-(o-hydroxyphenyl)ethyl]thiazolidine (16 g) m.p. 100°–102° C.

α-Chloroacetylchloride (13.4 g, 9.5 ml) is added, with exclusion of humidity, under stirring, in 30 minutes, to a solution of the above thiazolidone (12 g) in 1,2-dichloroethane (120 ml) and triethylamine (18 ml), cooled at −10° C. Stirring is continued for 1 hour at 0° C. and the mixture is partitioned with water. The organic phase is separated, washed with water, dried on $CaCl_2$ and the solvents are evaporated to dryness in vacuum. Crystallization from $Et_2O$ gives 3-α-chloroacetyl-2-[2'-(o-α-chloroacetoxy-phenyl)ethyl]thiazolidone (12 g), m.p. 88°–89° C. (hexane/AcOEt 7:3, $R_f$=0.5). A solution of this compound (6 g) in acetone (30 ml) is treated with potassium thioacetate (4.1 g) under stirring for 30 minutes. The mixture is filtered from the inorganic materials, the acetone is evaporated under vacuum and the residue is partitioned between water and EtOAc. From the organic phase after the usual work-up it is obtained 3-acetylthioacetyl-2-[2'-(o-acetylthioacetoxyphenyl)ethyl]thiazolidine as a colorless oil (hexane/AcOEt 7:3, $R_f$=0.4).

EXAMPLE 5

A solution of 3-chloroacetyl-2-[2'-(o-chloroacetoxyphenyl)ethyl]thiazolidine (5.5 g) in dry methanol is treated with p-toluensulphonic acid (0.5 g) at room temperature for 2 days. The excess of solvent is evaporated in vacuum and then the mixture is diluted with water (80 ml). The crystalline precipitate is collected by filtration, dried in vacuum and recrystallized from $Et_2O$ to give 3.9 g of 3-chloroacetyl-2-[2'-(o-hydroxyphenyl)ethyl]thiazolidine m.p. 98° C.

The same compound is obtained by treatment at −35° of a solution of 2-[2'-(o-hydroxyphenyl)ethyl]thiazolidine (5 g) in 1,2-dichloroethane (50 ml) with triethylamine (3.8 ml) and chloroacetylchloride (2 ml), which is added dropwise in 15 minutes.

The organic phase is warmed at room temperature, washed with water, dried on CaCl$_2$ and the solvents are evaporated in vacuum to dryness. The residue gives 4.5 g of 3-α-chloroacetyl-2-[2'-(o-hydroxyphenyl)ethyl]thiazolidine m.p. 96-98 (from Et$_2$O).

The obtained compound (3.5 g) is reacted in acetone (20 ml) with potassium thioacetate (1.5 g) at room temperature for 1 hour to give 3-acetylthioacetyl-2-[2'-(o-hydroxyphenyl)ethyl]thiazolidine (3.2 g), as a colourless oil (R$_f$ 0.25 hexane/EtOAc 6:4).

H-NMR=2.35 (s, 3H, —S—CO—CH$_3$); 3.7 (s, 2H, —CO—CH$_2$—S—CO—; 2.1-2.4 (2s, 4H, CH$_2$—CH$_2$); 7 (m, 4H,

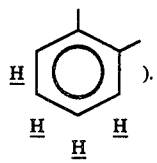

).

EXAMPLE 6

Chloroacetyl chloride (8.4 ml) is added dropwise to a stirred mixture of pyrocatechol (11 g), triethylamine (28 ml) and dry methylene chloride (100 ml), cooled at 0° C., in 20 minutes.

The mixture is warmed at room temperature, then heated to reflux for 2 hours. The organic phase is washed with water, 5% aqueous sodium hydroxyde and then with water. After drying on Na$_2$SO$_4$, the solvent is evaporated to dryness under vacuum and the crude material is crytallized from cyclohexane-Et$_2$O to give 1,4-benzodioxan-2-one (10 g) m.p. 52°-54° C. A molar solution of DIBAH in toluene (73 ml) is added dropwise to a stirred solution of 1,4-benzodioxan-2-one (8.9 g) in dry toluene (100 ml), cooled at −70° C. during 40 minutes. Stirring at this temperature is continued for 15 minutes, then the excess reagent is destroyed by adding 2N-isopropanol in toluene (75 ml), under stirring, at −70°÷−60° C. The mixture is warmed at room temperature and treated with 30% NaH$_2$PO$_4$ aqueous solution (6 ml) and 25 g of anhydrous Na$_2$SO$_4$, for 4 hours, under stirring. The inorganic material is filtered out and the eluate is evaporated to dryness to give 8.2 g of 2-hydroxy-1,4-benzodioxan. A stirred solution of this δ-lactol (7.8 g) in ethanol (30 ml) is treated with a solution of cysteamine hydrochloride (7.36 g) and potassium acetate (6.5 g) in water (12 ml). Stirring is continued for 45 minutes, then a crystalline precipitate of 2-[(o-hydroxyphenoxy)methyl]thiazolidine (8.1 g) is obtained. M.p. 76°-78° C.

EXAMPLE 7

Chloroacetylchloride (2.5 ml) is added to a stirred solution of 2-[(o-hydroxyphenoxy)methyl]thiazolidine (6 g) in 1,2-dichloroethane (80 ml) and triethilamine (4.3 ml) cooled at −30° C. After the usual work-up 3-α-chloroacetyl-2-[(o-hydroxyphenoxy)methyl]thiazolidine (5.7 g, from Et$_2$O, m.p. 89°-91° C.) is obtained. A stirred solution of the latter compound in 1,2-dichloroethane (50 ml) is heated with solid potassium thioacetate (4 g). After 2 hours, the mixture is washed with water to give, after the usual work-up, 3-acetylthio-acetyl-2-[(o-hydroxyphenoxy)methyl]thiazolidine (6.4 g, from EtOH) m.p. 97°-99° C.

A stirred solution of this compound (2.5 g) in dimethoxyethane (25 ml) is treated with 30% aqueous ammonia (5 ml) in inert gas atmosphere. Stirring is continued for 5 hours, the reagents are evaporated to small volume in vacuum and the residual mixture is diluted with 30% NaH$_2$PO$_4$ aqueous solution (25 ml). After extraction of the aqueous medium with Et$_2$O, the usual work-up gives 3-mercaptoacetyl-2-[(o-hydroxyphenoxy)methyl]thiazolidine (1.22 g) m.p. 92°-93° C.

EXAMPLE 8

A solution of 3-α-chloroacetyl-2-[2'-(o-hydroxyphenoxy)methyl]thiazolidine (1 g) in DMSO (5 ml) is treated at room temperature with sodium-imidazolyl (0.58 g). After 3 hours the mixture is poured in ice (20 g) and 30% NaH$_2$PO$_4$ aqueous solution (50 ml) and extracted with EtOAc. After the usual work-up, 3-(imidazol-1'-yl)acetyl-2-[(o-hydroxyphenoxy)methyl]thiazolidone (0.68 g) is obtained as a colourless oil.

A solution of this compound in Et$_2$O is treated with gaseous HCl and the crystalline hydrochloride (m.p. 170° C.) is obtained.

EXAMPLE 9

Following the procedure described in Example 7, but using an excess of α-chloro-acetylchloride, the following 2-substituted thiazoline are prepared:

3-α-chloroacetyl-2-[(o-α-chloroacetoxyphenoxy)methyl]thiazolidine; m.p. 88°-89° C.;

3-α-acetylthioacetyl-2-[(o-α-acetylthioacetoxyphenoxy)methyl]thiazolidine, as a colourless oil;

H-NMR=2.35 (2s, 6H, —S—CO—CH$_3$); 3.7-4 (2s, 4H, CH$_2$—S—); 5.5 (t, 1H,

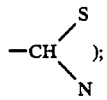

);

7 (s, 4H, H on benzene ring).

EXAMPLE 10

α-Ortho-tolyloxy-ethanal (7.8 g) is reacted in ethanol (30 ml) with an aqueous solution of cysteamine acetate (6.4 10$^{-2}$M). The mixture is stirred for 30 minutes at room temperature and poured in water (50 ml).

The precipitate is filtered and crystallized from petroleum ether/isopropyl ether (3:1) to give 2-(o-tolyloxymethyl)thiazolidine (7 g) m.p. 66°-68° C.

A solution of this compound (6.5 g) in dry 1,2-dichloroethane is cooled at 0° C. and treated with triethylamine (5 ml) and with α-chloroacetylchloride, added during 15 minutes. The mixture is stirred for additional 20 minutes, then solid potassium thioacetate is added. After 1 hour, the inorganic material is removed by filtration and the organic filtrate is washed with water.

After the usual work-up, the residual oil (13 g) is purified by column chromatography on SiO$_2$, using a mixture of petroleum ether-Et$_2$O 7:3 as the eluent.

The recovered 3-acetylthioacetyl-2-(o-tolyloxymethyl)thiazolidine (9.51 g) is a colourless oil, which can't be crystallized. H-NMR=2.2 (s, 3H,

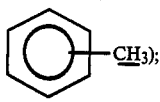

2.35 (s, 3H, S—CO—CH₃); 3.8 (d, 2H, O—CH₂—CH); 5.5 (t, 1H,

EXAMPLE 11

Using potassium thiobenzoate in the procedure of the Example 10, the 3-benzoylthioacetyl-2-[o-tolyloxymethyl]thiazolidine is obtained as an uncrystallizable colourless oil. 3-Mercaptoacetyl-[2-o-tolyloxymethyl]-thiazolidine m.p. 54°–56° C. is prepared by hydrolysis with aqueous ammonia, according to the procedure of the Example 7.

EXAMPLE 12

A solution of α-(o-methoxy)phenoxy ethanal (9 g) in ethanol (90 ml) is heated with a L-cysteine (6.71 g) solution in water (36 ml) and with acetic acid (5.4 ml), for a night at 50° C. After cooling at room temperature, the white precipitate is filtered out and crystallized from EtOAc to give 4-carboxy-2-(o-methoxyphenoxymethyl)thiazolidine (9.3 g) m.p. 149°–150° C. $[\alpha]_D = -86°$; $[\alpha]_{365°} = -226°$ (EtOH).

A solution of this compound (0.6 g) in dry acetone (10 ml) is heated with triethylamine (0.98 ml) and α-chloroacetylchloride (0.48 ml) for 2 hours at room temperature. Potassium-thioacetate (1.14 g) is then added to the mixture which is stirred for additional 3 hours at room temperature. The acetone is partially removed under vacuum and the mixture is diluted with water and acidified to pH 6.5. After extraction with ethylacetate and the usual work-up, 0.25 g of 4-carboxy-2-(o-methoxyphenoxymethyl)-3-acetylthioacetylthiazolidine is obtained as a colourless oil, $[\alpha]_D = -24°$ (EtOH).

EXAMPLE 13

Following the procedure described in Example 12, but using an aqueous solution of L-cysteine methyl ester hydrochloride and sodium acetate, 4-carbomethoxy-2-(o-methoxy)phenoxymethyl-thiazolidine $[\alpha]_D = -57°$ (EtOH) and 4-carbomethoxy-2-(o-methoxyphenoxymethyl)-3-acetylthioacetyl-thiazolidine $[\alpha]_D = -48°$ (EtOH) are prepared.

EXAMPLE 14

A mixture of [α-(o-methoxy)phenoxy]ethanal (7.9 g), L-cysteine ethyl ester (8.8 g), sodium acetate.3H₂O (7.1 g) and ethanol (200 ml) is stirred at room temperature for 12 hours. The excess solvent is evaporated and the mixture is diluted with water, extracted with EtOAc. The combined organic phases are washed with water, aqueous NaHCO₃, then water, dried and evaporated to dryness, to give an oil (13 g). Further crystallization from hexane gives 4-carbethoxy-2-(o-methoxyphenoxy)methyl-thiazolidine (12 g) m.p. 50° C.; $[\alpha]_D = -49°$ (EtOH). Subsequent treatment in acetone of this compound (8.5 g) with triethylamine (6.1 ml) and α-chloroacetylchloride (3.3 ml) and, without separation of the intermediate 1-α-chloroacetyl-thiazolidine, with potassium-thioacetate (6.5 g) gives, after the usual work-up, 4-carbethoxy-2-(o-methoxyphenoxy)methyl-3-acetylthioacetyl-thiazolidine (7 g) m.p. 90° (from Et₂O) $[\alpha]_D = -41°$ (EtOH).

EXAMPLE 15

The reaction of 4-carbethoxy-2-(o-methoxy)phenoxymethyl-thiazolidine (7.5 g) in dry methylene chloride with ethoxalylchloride (3.1 ml) in the presence of triethylamine (3.9 ml) for 2 hours at room temperature, gives 4-carbethoxy-2-(o-methoxyphenoxy)methyl-3-ethoxalyl-thiazolidine (8.5 g) as a colourless oil, $[\alpha]_D = -46°$ (EtOH) after the usual work-up.

EXAMPLE 16

Following the procedure described in Example 15, but using the ethoxysuccinoylchloride and the ethoxyglutaroylchloride, the following compounds are obtained:

4-carbethoxy-2-(o-methoxy-phenoxy)methyl-3-(3'-carbethoxy)propanoyl-thiazolidine $[\alpha]_D = -38°$ (EtOH);

4-carbethoxy-2-(o-methoxy-phenoxy)methyl-3-(4'-carbethoxy)butanoyl-thiazolidine $[\alpha]_D = -32°$ (EtOH).

EXAMPLE 17

Following the procedure described in Example 14, but using α-[(o-ethoxy)phenoxy]ethanal, α-[(o-propargyloxy)phenoxy]ethanal, α-[(o-allyloxy)phenoxy]ethanal and α-[(o-methoxy)phenylthio]ethanal the following compounds are obtained:

4-carbethoxy-2-(o-ethoxy-phenoxy)methyl-thiazolidine, $[\alpha]_D = -56°$ (EtOH);

4-carbethoxy-2-(o-ethoxy-phenoxy)methyl-3-α-acetylthioacetyl-thiazolidine, $[\alpha]_D = -39°$ (EtOH);

4-carbethoxy-2-(o-propargyloxy-phenoxy)methyl-thiazolidine, $[\alpha]_D = -81°$ (EtOH);

4-carbethoxy-2-(o-propargyloxy-phenoxy)methyl-3-α-acetylthioacetyl-thiazolidine, $[\alpha]_D = -71°$ (EtOH);

4-carbethoxy-2-(o-allyloxy-phenoxy)methyl-thiazolidine, $[\alpha]_D = -62°$ (MeOH);

4-carbethoxy-2-(o-allyloxy-phenoxy)methyl-3α-acetylthioacetyl-thiazolidine $[\alpha]_D = -66°$ (MeOH);

4-carbethoxy-2-(o-methoxy-phenylthio)methyl-thiazolidine $[\alpha]_D = -59°$ (MeOH);

4-carbethoxy-2-(o-methoxy-phenylthio)methyl-3α-acetylthioacetyl-thiazolidine $[\alpha]_D = -49°$ (MeOH);

4-carboxy-2-(o-methoxyphenyl)methyl-thiazolidine $[\alpha]_D = -75.5°$; $[\alpha]_{365} = -168°$ (MeOH).

EXAMPLE 18 o-Methoxy-thiophenol (83.5 g) is reacted in DMF (150 ml) with α-bromoethanal dimethyl acetale (76.2 ml) in the presence of dry K₂CO₃ (81.4 g), under stirring, in inert gas atmosphere for 2 hours at 50° C. The mixture is cooled and after filtration of the inorganic material it is diluted with water (500 ml) and extracted with Et₂O. The collected organic phases are dried on Na₂SO₄ and evaporated to dryness to give 85 g of α-(o-methoxyphenylthio)ethanal dimethyl acetal as a colourless oil.

A solution of this compound in methanol (400 ml) is treated with 2N H₂SO₄ (100 ml) for 2 hours at 80°, the excess methanol is evaporated in vacuum and the residue is diluted with water and extracted with Et₂O. The usual work-up gives α-(o-methoxyphenylthio)ethanal (70.2 g).

15.5 g of this latter substance is reacted in water (50 ml) with cysteamine hydrochloride (8 g) and potassium acetate (6.56 g), under stirring for 2 hours at room temperature. Addition of methylenechloride (30 ml) and the usual work-up of the organic phase give a crude oil (13 g) which is crystallized from isopropanol to yield 2-(o-methoxyphenylthio)methyl-thiazolidine m.p. 111°–112° C.

Using in this procedure α-(o-methoxy-phenoxy)ethanal, α-(o-ethoxyphenoxy)ethanal, α-(o-allyloxyphenoxy)ethanal and α-(o-propargyloxyphenoxy)ethanal the following 2-substituted thiazolidines are obtained:

2-(o-ethoxyphenoxymethyl)thiazolidine m.p. 60°–64° C.;

2-(o-methoxyphenoxymethyl)thiazolidine m.p. 62°–63° C.;

2-(o-allyloxyphenoxymethyl)thiazolidine m.p. 55°–56° C.;

2-(o-propargyloxyphenoxymethyl)thiazolidine m.p. 72°–74° C.

EXAMPLE 19

A solution of 2-(o-methoxyphenoxymethyl)thiazolidine (100 g) in 1,2-dichloroethane (250 ml) cooled at 10° is heated, under stirring, with triethylamine (68 ml) and a solution of α-chloroacetylchloride (36.2 ml) in 1,2-dichloroethane (50 ml) is added dropwise. After 1 hour, the mixture is washed with water, dried on Na₂SO₄ and evaporated to dryness. Subsequent crystallization from propan-2-ol gives 3-α-chloroacetyl-2-(o-methoxyphenoxymethyl)thiazolidine m.p. 87°–88° C. (100 g).

EXAMPLE 20

A solution of 2-(o-methoxyphenoxymethyl)thiazolidine (15 g) in acetone (75 ml), cooled at 10° C., under stirring is added with triethylamine (10.5 ml) and dropwise with a solution of α-chloroacetylchloride (5.8 ml) in acetone (15 ml). After 2 hours the mixture is added with potassium thioacetate (35.4 g) and stirring is continued for 2 hours, the mixture is poured in ice and water (250 ml) and the precipitate is filtered and crystallized from EtOH to give 2-(o-methoxyphenoxy)methyl-3-acetylthioacetylthiazolidine (19.8 g, 87% yield) m.p. 89°–91° C.

EXAMPLE 21

A solution of 3-α-chloroacetyl-2-(o-methoxyphenoxy)methyl-thiazolidine (6 g) in acetone (80 ml) is heated to reflux temperature in the presence of sodium iodide (5 g) for 3 hours and then poured in ice and water (400 ml). The precipitate is collected, dissolved in methylene dichloride and washed with water, 5% aqueous NaHCO₃, 2N sodium thiosulphate, water and dried on Na₂SO₄. After the usual workup, the residue is crystallized from acetone and isopropanol to give 5.92 g of 3-α-iodoacetyl-2-(o-methoxyphenoxy)methyl-thiazolidine m.p. 81°–83° C. Using in this procedure sodium bromide, the 3-α-bromoacetyl-2-(o-methoxyphenoxy)methyl-thiazolidine is obtained, m.p. 82°–84° C.

EXAMPLE 22

A solution of a 3-α-haloacetyl-2-(o-methoxyphenoxy)methyl-thiazolidine (for example the 1-α-bromoacetyl, 2.07 g) in 1,2-dichloroethane (20 ml) is treated under stirring with 3,4,5-trimethoxy-thiobenzoic acid (m.p. 172°–174° C. obtained from 3,4,5-trimethoxy-benzoylchloride and NaSH in aqueous ethanol) in the presence of aqueous solution of potassium carbonate (2 g) and tetrabutylammonium bromide (0.32 g). After a night, the organic phase is separated, washed with water, dried on CaCl₂. After the usual work-up and filtration on short column of SiO₂ with hexane/AcOEt 3:1, 3-(3',4',5'-trimethoxy-benzoyl)thioacetyl-2-(o-methoxyphenoxy)methyl-thiazolidine (2.2 g) is obtained, m.p. 110°–112° C.

Using in this procedure the thiobenzoic acid and the thionicotinic acid, the following compounds are obtained;

3-benzoylthioacetyl-2-(o-methoxyphenoxy)methyl-thiazolidine, m.p. 84°–86° C.;

3-nicotinoylthioacetyl-2-(o-methoxyphenoxy)methyl-thiazolidine m.p. 89°–91° C., hydrochloride m.p. 138°–139°, methansulphonate m.p. 122°–124° C.

EXAMPLE 23

Under an inert gas athmosphere, 30% ammonium hydroxyde (10 ml) is added to a stirred solution of 3-acetylthioacetyl-2-(o-methoxyphenoxy)methyl-thiazolidine (3.5 g) in 1,2-dimethoxyethane (20 ml). After 2 hours the mixture is diluted with water (120 ml) and the precipitate is filtered, dried under vacuum, crystallized from ethyl ether to give 3-mercaptoacetyl-2-(o-methoxyphenoxy)methyl-thiazolidine (2.4 g) m.p. 86°–87° C.

A solution of this compound (0.8 g) in dry pyridine (3.2 ml) is treated with cyclopentylpropionyl-chloride (0.5 g). After a night, the mixture is diluted with 2N, H₂SO₄, extracted with Et₂O to afford after the usual work-up 3-(3'-cyclopentyl)propionylthioacetyl-2-(o-methoxyphenoxy)methyl-thiazolidine (0.92 g) m.p. 48°–49° C.

In the same way, using 3-cyclohexylpropionylchloride, 3-phenylpropionylchloride and cyclopropylcarbonylchloride instead of 3-cyclopentylpropionylchloride the following compounds are obtained:

3-(3'-cyclohexyl)propionylthioacetyl-2-(o-methoxyphenoxy)methyl-thiazolidine, m.p. 44°–45° C.;

3-(3'-phenyl)propionylthioacetyl-2-(o-methoxyphenoxy)methyl-thiazolidine, m.p. 38°–44° C.;

3-(cyclopropylcarbonylthioacetyl)-2-(o-methoxyphenoxy)methyl-thiazolidine, m.p. 99°–101° C.

EXAMPLE 24

Following the procedure of Example 23, but using phenoxyacetylchloride, ethoxyoxalylchloride, ethoxycarbonylchloride, the following thiazolidines are obtained:

3-phenoxyacetylthioacetyl-2-(o-methoxyphenoxy)-methyl-thiazolidine m.p. 64°–66° C.;

3-ethoxalylthioacetyl-2-(o-methoxyphenoxy)methyl-thiazolidine m.p. 64°–66° C.;

3-ethoxycarbonylthioacetyl-2-(o-methoxyphenoxy)-methyl-thiazolidine m.p. 72°–76° C.

EXAMPLE 25

A solution of 2-(o-methoxyphenoxy)ethanal (0.45 g) in ethanol (10 ml) and few drops of acetic acid are added to a solution of L-penicillamine (3-mercapto-D-valine, 0.45 g) in ethanol (20 ml), the mixture is stirred at room temperature for 3 hrs. The solvent is evaporated in vacuum to a small volume, the residue is diluted with water and extracted with ethylacetate. After the usual work-up, the residual oil is crystallized from ethanol to give 2-(o-methoxyphenoxy)methyl-4,4-dimethyl-5-carboxy-thiazolidine m.p. 136°-138° C.

In similar way, starting from 3-mercapto-D-valine ethylester, the following compounds are obtained:
2-(o-methoxyphenoxy)methyl-4,4-dimethyl-5-carbethoxy-thiazolidine [α]$_D$=+13° (MeOH); and
3-acetylthioacetyl-2-(o-methoxyphenoxy)methyl-4,4-dimethyl-5-carbethoxy-thiazolidine [α]$_D$=+24° (MeOH).

EXAMPLE 26

A monoperphtalic acid solution (41 ml, 66.5 mg/ml) in ethyl acetate is added to a stirred solution of 3-chloroacetyl-2-(o-methoxyphenoxy)methyl-thiazolidine (7 g) in ethyl acetate cooled at 0° C. After 2 hours the mixture is washed with 5% aqueous NaHCO$_3$, aqueous sodium sulphite, 5% aqueous NaHCO$_3$ and water. The organic phase is dried on Na$_2$SO$_4$ and the solvent is evaporated to dryness in vacuum. The residue is crystallized from ethanol to give 3-chloroacetyl-2-(o-methoxyphenoxy)methyl-thiazolidine-1-sulphoxide. (5.62 g) m.p. 127°-128° C.

A solution of this sulphoxide (4.68 g) in 1,2-dichloroethane (40 ml) is reacted with dry potassium-thioacetate (2 g) for 2 hours at room temperature under stirring. After the usual work-up 3-acetylthioacetyl-2-(o-methoxyphenoxy)methyl-thiazolidine-1-sulphoxide is obtained, m.p. 112°-114° C.

EXAMPLE 27

Following the procedure described in Example 22, but using 3-chloroacetyl-2-(o-methoxyphenoxy)methyl-thiazolidine-1-sulphoxide, the following thiazolidines are prepared:
3-benzoylthioacetyl-2-(o-methoxyphenoxy)methyl-thiazolidine-1-sulphoxide m.p. 110°-112° C.;
3-(3,4,5-trimethoxybenzoyl)thioacetyl-(2-o-methoxyphenoxy)methyl-thiazolidine-1-sulphoxide m.p. 122°-124° C.

EXAMPLE 28

Imidazolyl sodium (3.58 g) is added to a stirred solution of 3-chloroacetyl-2-(o-methoxyphenoxy)methyl-thiazolidine (5.8 g) in DMSO (35 ml). After 1 hour the mixture is poured in ice and water (200 ml) and the separated oil is extracted with EtOAc (3×30). The organic phases are collected, washed with water, dried on Na$_2$SO$_4$. After evaporation, the crude residue is purified by filtration on a short column of SiO$_2$ using EtOAc and EtOAc/MeOH 85:15 as the eluent to give 3-(imidazol-1-yl)acetyl-2-(o-methoxyphenoxy)methyl-thiazolidine (5.1 g) as a colourless oil.

A stirred solution of this compound in isopropanol (25 ml) and Et$_2$O (35 ml) is treated with 7,7N aqueous nitric acid (2.1 ml). After 2 hours the crystalline precipitate is collected by filtration, washed with Et$_2$O (30 ml) and dried under vacuum to give 3-(imidazol-1-yl)acetyl-2-(o-methoxyphenoxy)methyl-thiazolidine nitrate, m.p. 139°-140° C.

EXAMPLE 29

Potassium carbonate (3.8 g) and N-methylpiperazine (3.2 g) are added to a stirred solution of 3-chloroacetyl-2-(o-methoxyphenoxy)methyl-thiazolidine (8 g) in acetonitrile (48 ml). The mixture is heated to reflux temperature for 1 hour, the excess solvent is removed in vacuum and the residue is partitioned between water and EtOAc. The usual work-up gives 5.5 g of 3-(4'-methyl-piperazin-1'-yl)acetyl-2-(o-methoxyphenoxy)methyl-thiazolidine as a colourless oil.

Its hydrochloride (m.p. 212°-214°) is formed and crystallized from 2-propanol.

EXAMPLE 30

Following the same procedure described in Example 29, using the following amines: morpholine, piperidine, N-m-chlorophenylpiperazine, N-phenylpiperazine; the following thiazolidines are obtained:
3-morfolylacetyl-2-(o-methoxyphenoxy)methyl-thiazolidine hydrochloride m.p. 88°-88.5° C.;
3-piperidyl-2-(o-methoxyphenoxy)methyl-thiazolidine as a colourless oil, hydrochloride 90°-92° C.;
3-(4'-m-chlorophenyl-piperazin-1'-yl)-2-(o-methoxyphenoxy)methyl-thiazolidine as a colourless oil, bis methanesulphonate m.p. 60° C., bis.HCl m.p. 178°-180° C.;
3-(4'-phenylpiperazin-1'-yl)-2-(o-methoxyphenoxy)-methyl-thiazolidine m.p. 52°-54° C.; hydrochloride 134°-136° C.

EXAMPLE 31

To a cooled solution of N-methylpiperazino acetic acid (1.73 g) and triethylamine (1.52 ml) in dichloromethane is added a solution of isobutylchloroformate (1.44 ml) in dichloromethane (6 ml). The mixture is stirred for 45 minutes at −10° C., then 3-mercaptoacetyl-2-(o-methoxyphenoxy)methyl-thiazolidine (3.4 g) dissolved in dichloromethane (10 ml) is added. The mixture is kept for 45 minutes at −10° C. then it is warmed at room temperature.

After the usual work-up, 3-(4'-methylpiperazine-1-yl)acetylthioacetyl-2-(o-methoxyphenoxy)methyl-thiazolidine is obtained as vitreous oil.

A solution of this compound (4.78 g) in acetone (25 ml) is treated with gaseous HCl: its bis.hydrochloride, precipitates with m.p: 178°-180° C. Using in this procedure morfolinoacetic, 4-m-chlorophenyl-piperazinoacetic, N,N-diethylaminoacetic acids, the corresponding thiazolidines are obtained:
3-(1-morfolyl)acetylthioacetyl-2-(o-methoxyphenoxy)-methyl-thiazolidine m.p. 165°-168° C. (as HCL salt);
3-diethylaminoacetylthioacetyl-2-(o-methoxyphenoxy)-methyl-thiazolidine m.p. 142°-150° C. (as HCl salt);
3-(4'-m-chlorophenyl)acetylthioacetyl-2-(o-methoxyphenoxy)methyl-thiazolidine m.p. 182°-186° C. (as HCl salt).

EXAMPLE 32

α-Bromopropionylchloride (0.97 ml) in methylene chloride (15 ml) is added dropwise to a mixture of 2-(o-methoxyphenoxy)methyl-thiazolidine (2 g) and triethylamine (1.35 ml) in CH$_2$Cl$_2$ (30 ml) at 0°-5° C. After 1 hour, the mixture is washed with water and the usual work-up gives 3-α-bromopropionyl-2-(o-methoxyphenoxy)methyl-thiazolidine as a colourless oil.

The compound is reacted with an excess of potassium-thioacetate (1.8 g) in acetone (15 ml) to give after the usual work-up, 3-(acetylthio)propionyl-2-(o-methoxyphenoxy)methyl-thiazolidine (1.8 g) as an uncrystallizable oil. After 2 months, this sample, maintained at −20° C., shows some crystalline seeds. Further crystallization from Et$_2$O give 0.83 g of a diasteroisomeric couple m.p. 101°-102° (SS,RR) and an uncrystallizable oil (SR, RS). Even though the absolute configurations of the chiral center have been defined on the basis of H-NMR spectra, they cannot be considered definitively ascertained.

EXAMPLE 33

A solution of 2-(o-methoxyphenylthio)methyl-thiazolidine (5 g) in pyridine (25 ml) is reacted with acetylthioacetylchloride (2.93 g) for a night at room temperature, the reaction mixture is diluted with 2N H$_2$SO$_4$, extracted with ethylether to give after the usual work-up 3α-acetylthioacetyl-2-(o-methoxyphenylthio)-methyl-thiazolidine, m.p. 62°–64° C.

In a similar way the following compounds are obtained:

2-(o-ethoxyphenoxy)methyl-3-acetylthioacetylthiazolidine;

2-(o-allyloxyphenoxy)methyl-3-acetylthioacetyl-thiazolidine;

2-(o-propargyloxyphenoxy)methyl-3-acetylthioacetyl-thiazolidine;

4-carboxy-2-(o-methoxyphenylthio)methyl-3-acetylthioacetyl-thiazolidine $[\alpha]_D = -39°$ (MeOH).

EXAMPLE 34

A solution of 2-(o-methoxyphenoxy)methyl-thiazolidine (1.83 g) in pyridine (6 ml) is treated with methane sulphonyl chloride (1.2 g) at room temperature. After 4 hours the mixture is diluted with 2N H$_2$SO$_4$, extracted with Et$_2$O, to afford after the usual work-up 2.2 g of 3-methanesulphonyl-2-(o-methoxypheoxy)methyl-thiazolidine m.p. 118°–120° C.

EXAMPLE 35

Following the procedure described in Example 34, but using the following acylating agents: p-toluensulphonylchloride, benzensulphonylchloride, acetic anhydride, trifluoroacetic anhydride, succinic anhydride; glutaric anhydride, cyclopropylcarbonylchloride, ethoxyoxalylchloride, the following thiazolidines are obtained:

3-p-tolylsulphonyl-2-(o-methoxyphenoxy)methyl-thiazolidine m.p. 131°–133° C.;

3-phenylsulphonyl-2-(o-methoxyphenoxy)methyl-thiazolidine m.p. 124°–126° C.;

3-acetyl-2-(o-methoxypheoxy)methyl-thiazolidine m.p. 84°–85° C.;

3-trifluoroacetyl-2-(o-methoxyphenoxy)methyl-thiazolidine m.p. 78°–81° C.;

3-(β 3'-carboxy-propionyl)-2-(o-methoxyphenoxy)-methyl-thiazolidine m.p. 122°–124° C.;

3-(4'-carboxy-butirroyl)-2-(o-methoxyphenoxy)methyl-thiazolidine m.p. 122°–124° C.;

3-ethoxyoxalyl-2-(o-methoxyphenoxy)methyl-thiazolidine m.p. 88°–91° C.;

3-cyclopropylcarbonyl-2-(o-methoxyphenoxy)methyl-thiazolidine m.p. 82°–83° C.

EXAMPLE 36

Reaction in pyridine (5 ml) of 2-(o-methoxyphenoxy)methyl-thiazolidine (0.9 g) with α-bromo-isobutirroylchloride (0.54 ml) for 30 minutes at 0° C. followed by 2 hours at room temperature gives 2-(o-methoxyphenoxy)methyl-3α-(2'-bromo-2'-methylpropionyl)-thiazolidine as an oil.

H-NMR = 1.6 (6H, 2S,

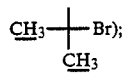

3.5 (3H, S, OCH$_3$).

EXAMPLE 37

A solution of α-(o-methoxyphenylthio)ethanal dimethylacetal (6.2 g), cysteamine hydrochloride (4.6 g) and potassium acetate (3.92 g) in 70% aqueous acetic acid is heated for 2 hours at 100° C. The mixture is poured in an excess of 7% aqueous sodium hydrogenocarbonate and ice and the precipitate is collected by filtration affording, after crystallization from acetone-isopropylether, 5 g of 2-(o-methoxypheylthio)methyl-thiazolidine m.p. 111°–112° C.

Subsequent treatment with α-chloroacetylchloride gives 3α-chloroacetyl-2-(o-methoxyphenylthio)methyl-thiazolidine m.p. 127°–129° C. which is converted by treatment with potassium thioacetate into 3-acetylthioacetyl-2-(o-methoxyphenylthio)methyl-thiazolidine oil; H-NMR (CDCl$_3$): 7 (m, 4H, Arom); 3.95 (s, 3H, OCH$_3$); 3.8 (d, 2H, S—CHHD 2—); 2.4 (s, 3H,

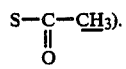

Starting from the same α-chloroacetyl compound (1.65 g) by reaction in acetonitrile with 4-methylpiperazine (1.5 ml) in the presence of potassium carbonate (1.5 g) for a night at room temperature, after the usual work-up 3-(4'-methylpiperazin-1'-yl)acetyl-2-(o-methoxyphenylthio)methyl-thiazolidine is obtained m.p. 144°–146° C.; bis-hydrochloride salt m.p. 203°–205° C.

Starting from the 3-(acetylthioacetyl-2-(o-methoxyphenoxy)methyl-thiazolidine by ammonolysis, according to the procedure of Example 23, an subsequent esterification with 4-methyl-piperazin-1-yl-acetic acid mixed anhydride 3-(4'-methylpiperazin-1'-yl)acetylthioacetyl-2-(o-methoxyphenylthio)methyl-thiazolidine, free base is obtained as an oil; bis-hydrochloride m.p. 165°–169° C.

EXAMPLE 38

A solution of 3α-iodoacetyl-2-(o-methoxyphenoxy)-methyl-thiazolidine (3.9 g) in benzene (25 ml) is treated with triphenylphosphine (2.7 g) at the reflux temperature for 2 hours. The solution is cooled at room temperature and the crystalline compound formed is separated by filtration to give 4.2 g of 3-triphenylphosphonum acetyl-2-(o-methoxyphenoxy)methylthiazolidine iodide m.p. 165°–171° C.

Starting from the 3-chloro compound, the corresponding triphenylphosphonium chloride (m.p. 174°–177° C.) is obtained.

This latter (5.5 g) is dissolved in water (30 ml) and methylene chloride (30 ml) is added. The mixture is vigorously stirred and 0.1N sodium hyroxyde is added until a persistent light red color is developed in the presence of phenolphtalleine. The organic phase is separated, washed with water, dried and evaporated to dryness to yield 4.1 g (from ethylacetate) of 3-triphenylphosphilydenemethylcarbonyl-2-(o-methoxypheoxy)-methylthiazolidine m.p. 131°–135° C.

3 Grams of this ylide is treated in dimethoxyethane (12 ml) with 4-acetoxy-3-methoxy-benzaldehyde (1.16 g) for 3 hrs at room temperature. The mixture is evaporated to dryness and filtered on short SiO$_2$ column using as the eluent hexane-AcOEt 15:10 to give pure 3-E(4'-acetoxy-3'-methoxy)cinnamoyl-2-(o-methoxyphenoxy)-methyl-thiazolidine-)as an oil; H-NMR: 2.3 (s, 3H, CO$\underline{CH}_3$); 3.7 (s, 3H,

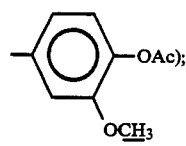

3.9 (s, 3H,

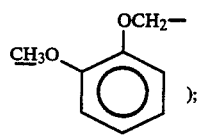

7.1-7.8 (m, 2H,

).

A solution of 0.8 g of this latter compound in dry ethanol (5 ml) is treated at room temperature with finely powdered K$_2$CO$_3$ (0.2 g), for a night, under stirring. The inorganic material is filtered out and the mixture is poured in water, extracted with ethylacetate affording, after the usual work-up, 0.7 g of 3-E(4'-hydroxy-3'-methoxy)cinnammoyl-2-(o-methoxyphenoxy)methyl-thiazolidine, oil, H-NMR: 3.7 (s, 3H,

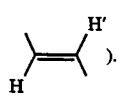

3.9 (s, 3H,

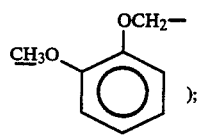

7.8-7.1 (m, 2H,

).

Following the same procedure, but using 3,4-diacetoxy-benzaldehyde the following compounds are prepared:
3-E(3',4'-diacetoxy)cinnamoyl-2-(o-methoxyphenoxy)-methyl-thiazolidine; H-NMR: 2.28 (s, 6H,

3.88 (s, 3H, O$\underline{CH}_3$); 7.88-7.05 (m, 2H,

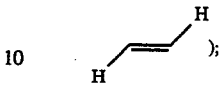

3-E(3',4'-dihydroxy)cinnamoyl-2-(o-methoxyphenoxy)-methyl-thiazolidine; H-NMR: 3.88 (s, 3H, —O$\underline{CH}_3$); 6.9 (s, 4H,

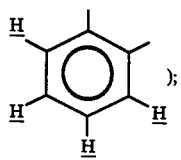

7.1 (s, 3H,

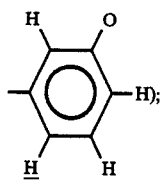

7.88-7.05 (m, 2H,

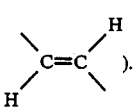).

EXAMPLE 39

To a solution of 3α-chloroacetyl-2-[2'-(o-hydroxyphenyl)ethyl]-thiazolidine (2.5 g) in methylene chloride (15 ml), 1,2-dihydropyrane (1 g) and p-toluensulphonic acid (50 mg) are added. The mixture is stirred for 2.5 hours at room temperature then pyridine (0.1 g) is added and the solvent is evaporated under vacuum. According to the procedure of Example 8, the residue is dissolved in DMSO and heated with imidazolyl sodium. After the usual work-up the intermediate 3-(imidazol-1-yl)acetyl-2-[2'-(o-hydroxyphenyl)ethyl]-thiazolidine-2''-tetrahydropyranylether (2.4 g) obtained is treated with 2N methanolic hydrochloric acid solution and the crystalline 3-(imidazol-1-yl)acetyl-2-[2'-(o-hydroxyphenyl)ethyl]-thiazolidine hydrochloride, m.p. 178°–181° C. is precipitated by dilution of the mixture with ethylether.

EXAMPLE 40

A solution of 2-(o-methoxyphenoxy)methyl-thiazolidine (0.98 g) in pyridine (4 ml) is reacted with succinic anhydride (0.4 g) for 2 hours at room temperature. The mixture is diluted with 2N aqueous sulphuric acid until pH 4.5, then with water. The crystalline precipitate is filtered and crystallized from aqueous ethanol to give 2-(o-methoxyphenoxy)methyl-3-(3'-carboxy)propionyl-thiazolidine (0.95 g) m.p. 104°–107° C.

In similar way, using benzoylchloride, 3,4,5-trimethoxybenzoylchloride, nicotinoylchloride and 3-carboethoxy-propionylchloride the following 3-acetyl-thiazolidines are obtained:

2-(o-methoxyphenoxy)methyl-3-(3'-carbethoxy)propionyl-thiazolidine, oil, H-NMR (CDCl$_3$): 6.90 (s, 4H, arom.); 3.8 (s, 3H, OC$\underline{H}_3$); 4.15 (q, 2H, C$\underline{H}_2$CH$_3$); 5.7 (t, 1H,

1.35 (t, 3H, CH$_2$—C$\underline{H}_3$);
2-(o-methoxyphenoxy)methyl-3-benzoyl-thiazolidine m.p. 74°–76° C.;
2-(o-methoxypheoxy)methyl-3-(3',4',5'-trimethoxy)-benzoyl-thiazolidine, oil, H-NMR (CDCl$_3$) 6.8 (s, 4H, arom.); 6.75 (s, 2H, arom.); 5.75 (t, 1H,

3.75 (s, 12H, 4 OCH$_3$);
2-(o-methoxyphenoxy)methyl-3-nicotinoyl-thiazolidine m.p. 98°–100° C.

EXAMPLE 41

Tert-butylcarbonate (19.3 g) is added to a stirred solution of 2-[2'-(O-hydroxyphenyl)ethyl]thiazolidine (18.5 g) in dimethylformamide (20 ml) at room temperature. After 1 hour, the mixture is diluted with water (200 ml) and the crystalline precipitate is filtered out to give 2-[2'-(O-hydroxyphenyl)ethyl]-3-BOC-thiazolidine (26.5 g), m.p. 113°–114° C.

In similar way the following BOC-thiazolidine are prepared:
2-[2'-(O-hydroxyphenyl)ethyl]-3-BOC-4-carboethoxy-thiazolidine, oil, H-NMR (CHCl$_3$-THMS): 1.3 (3H, t, CH$_2$—C$\underline{H}_3$); 1.5 (9H, s, —C(CH$_3$)$_3$); 3.3 (2H, d, s); 4.3 (2H, q, C$\underline{H}_2$—CH$_3$); 6.7–7.2 (4H, m);
2-(2'-O-hydroxyphenoxy)methyl-3-BOC-thiazolidine, m.p. 110° C.;
2-(2'-O-hydroxyphenoxy)methyl-3-BOC-4-carbethoxy-thiazolidine, oil H-NMR (CHCl$_3$-THMS): 1.5 (9H, s, —C(C$\underline{H}_3$)$_3$).

EXAMPLE 42

A solution of 2-(2'-O-hydroxyphenoxy)methyl-3-BOC-thiazolidine (1 g) in anhydrous DMF (10 ml) is stirred with 0.3 ml of allyl bromide and potassium carbonate (1 g) for 5 hours. After dilution with water (100 ml) and extraction with ethyl ether (2×30 ml), the organic phases are washed with water, dried on Na$_2$SO$_4$ and evaporated to dryness.

The residue 2-(2'-O-allyloxyphenoxy)methyl-3-BOC-thiazolidine (oil:H-NMR (CDCl$_3$-THMS): 1.4 (9H, s, C(C$\underline{H}_3$)$_3$; 4.55 (2H, d, —C$\underline{H}_2$—CH=); 5.6–5 (3H, m, C$\underline{H}_2$,

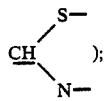

6.4–5.6 (1H, m, —C$\underline{H}$=) is treated in dichloromethane (5 ml) with trifluoroacetic acid (4 ml) and stirred for 1 hour at room temperature. The mixture is evaporated to dryness in vacuum, the residue is partitioned between 5% aqueous KHCO$_3$ and dichloromethane to give, after the usual work-up 2-(2'-O-allyloxyphenoxy)methyl-thiazolidine, m.p. 49°–51° C. An analytical sample has m.p. 55°–56° C.

Using in the same procedure the propargyl chloride, the following derivatives are prepared:
2-(2'-O-propargyloxyphenoxy)methyl-3-BOC-thiazolidine, m.p. 83°–85° C.;
2-(2'-O-propargyloxyphenoxy)methyl-thiazolidine, m.p. 78°–79° C. (from ethanol).

EXAMPLE 43

A solution of 3-morpholinomethyl-4-hydroxy-5-methoxy-benzaldehyde (5.02 g) in ethylacetate (50 ml) is treated with 3-triphenylphosphilydene-methylcarbonyl-2-(O-methoxyphenoxy)-methyl-thiazolidine (11.8 g) at room temperature. After 2 days, the mixture is extracted with 12% aqueous HCl (5×50 ml). The combined aqueous extracts are treated with 20% aqueous NaOH until pH 5 and then with 5% aqueous NaHCO$_3$ until pH 7.8–8, extracted with dichloromethane (2×25 ml) to give a crude material which is purified by SiO$_2$ column chromatography (hexane:ethylacetate 1:1).

The oil (5.3 g) is treated in ethylacetate with 6N HCl in isopropanol to give 3-(3'-morpholinomethyl-4'-hydroxy-3'-methoxy-cinnamoyl)-2-(O-methoxyphenoxy)methylthiazolidine hydrochloride (4.9 g) m.p. 124°–126° C.

In similar way the following compounds are prepared:
3-(3'-pyrrolidylmethyl-4'-hydroxy-5'-methoxy-cinnamoyl)-2-(O-methoxyphenoxy)methyl-thiazolidine-hydrochloride, m.p. 134°–136° C.;
3-(3'-morpholinomethyl-4'-hydroxy-5'-methoxy-cinnamoyl)2-(O-hydroxyphenoxy)methyl-thiazolidine maleate;
3-(3'-diethylaminomethyl-4'-hydroxy-5'-methoxycinnamoyl)-2-(O-propargyloxyphenoxy)methyl-thiazolidine-hydrochloride.

EXAMPLE 44

Using in the procedure of the Example 3 the following aldehydes:
2-(4-methyl-piperzin-1'-yl)ethanal
2-(morpholin-1'-yl)ethanal
3-(morpholin-1'-yl)propanal and propanal
the following 3-substituted thiazolidines are prepared:
3-[4-(4-methylpiperazin-1-yl)-2-butenoyl]-2-(O-methoxyphenoxy)methyl-thiazolidine maleate;
3-[4-(morpholin-1-yl)-2-butenoyl]-2-(O-methoxyphenoxy)methyl-thiazolidine-hydrochloride;
3-[5-(morpholin-1-yl)-2-pentenoyl]-2-(O-metoxyphenoxy)methyl-thiazolidine-hydrochloride;
3-(2-pentenoyl)-2-(O-methoxyphenoxy)methyl-thiazolidine.

EXAMPLE 45

A solution of acryloylchloride (12.2 ml) in $CH_2Cl_2$ is added to a stirred solution of 2-(O-methoxyphenoxy)-methyl-thiazolidine (30.5 g) and triethylamine (20.7 ml) in $CH_2CL_2$ (130 ml), cooled at 0°–5° C. The mixture is kept for 3 hours at 0°–5° C., the triethylamine hydrocloride is removed by filtration and the eluate is washed with water, 5% aqueous $NaHCO_3$, water. After drying on $Na_2SO_4$, and evaporation of the solvent, the crude residue is crystallized from ethylacetate to give 3-acryloyl-2-(O-methoxyphenoxy)methylthiazolidine m.p. 56°–58° C. Using in the procedure the 2-(O-hydroxypheoxy)methyl-thiazolidine and cooling the reaction mixture at −15°−−10° C., the 3-acryloyl-2-(O-hydroxyphenoxy)methyl-thiazolidine is obtained. A solution of these acryloylthiazolidines (1.1 g) in ethanol (20 ml) are treated with (2-hydroxyethylamino)ethylamine (0.42 ml).

The reaction mixture is kept for 28 hours at room temperature and evaporated to dryness. The residue is partitioned between water and ethylacetate. The organic phase is separated, washed with water, dried on $Na_2SO_4$ and evaporated to dryness.

A solution of the residual oil (1.6 g) in dry acetone (20 ml) is treated with a solution of maleic acid (0.48 g) in acetone (6 ml) to give a crystalline precipitate, yielding:
3-(3-(2-hydroxyethylamino)ethyl)aminopropanoyl-2-((O-methoxyphenoxy)methyl-thiazolidine bis maleate m.p. 128°–130° C.;
3-(3-(2-hydroxyethylamino)ethyl)aminopropanoyl-2-(O-hydroxymethyl)thiazolidine bis maleate m.p. 134°–136° C.;
3-(3-(2-hydroxyethylamino)ethyl)aminoprropanoyl-2-(O-propargyloxy-methyl)thiazolidine bis maleate.

EXAMPLE 46

In inert gas atmosphere, cysteamine hydrochloride (0.38 g) is treated with 2-(O-methoxyphenoxymethyl)-3-acryloyl-thiazolidine (0.8 g) in ethanol (25 ml) for 12 hours at room temperature and then for 8 hours at reflux temperature.

The reaction mixture is cooled at room temperature and after two days the crystalline precipitate is filtered to give 0.62 g of 3-(5-amino-4-thia-hexanoyl)-2-(O-methoxyphenoxy)methyl-thiazolidine-hydrochloride m.p. 116°–118° C.

Using in the same procedure N-acetyl-cysteine, in the presence of catalytic amount of sodium methylate, 3-(5-carboxy-5-acetylamino-4-thia-hexanoyl)-2-(O-methoxyphenoxy)methyl-thiazolidine m.p. 119°–121° C., is prepared.

EXAMPLE 47

By treatment of the above described acryloythiazolidine in ethanol with imidazole, the following compounds are prepared:
3-(3-imidazol-1-yl)-propionyl-2-(O-propargyloxyphenoxy)methyl-thiazolidine;
3-(3-imidazol-1-yl)-propionyl-2-(O-methoxyphenoxy)-methylthiazolidine m.p. 115°–117° C. (as nitrate).

EXAMPLE 48

A solution of 2-morpholine-ethylchloride hydrochloride (0.18 g) in water (5 ml) is added to a solution of 3-(2-mercaptoacetyl)-2-(O-methoxyphenoxy)methyl-thiazolidine in aqueous N sodium hydroxyde (10 ml), in inert gas atmosphere and stirred overnight at room temperature.

The aqueous phase is extracted with ethylether, and the combined organic phase are collected, washed with NaOH, water, dried on $Na_2SO_4$ and evaporated to dryness to give 3-[5-(morpholin-1-yl)-3-thia-pentanoyl)-2-(O-methoxyphenoxy)methyl-thiazolidine (oil), hyrochloride m.p. 158°–160° C.

EXAMPLE 49

A solution of 1-iodo-pentane (0.21 ml) in methanol (2 ml) is added to a solution of 3-(2-mercaptoacetyl)-2-(O-methoxyphenoxy)methyl-thiazolidine (0.5 g) in a sodium methylate solution (from 42 mg of sodium in 10 ml of methanol). The mixture is stirred for 3 hours at room temperature, diluted with N aqueous sodium hydroxide (60 ml) and then extracted with ethylacetate to give, after the usual work-up, 0.44 g of 3-(3-thia-octanoyl)-2-(O-methoxyphenoxy)methyl-thiazolidine oil. Using in this procedure the α-bromomethylacetate as alkylating agent, the 3-(4-carbomethoxy-3-thia-succinoyl)-2-(O-methoxyphenoxy)methylthiazolidine, m.p. 77°–79° C., is obtained.

EXAMPLE 50

A solution of dicyclohexylcarbodiimide (1.75 g) in dimethylformamide (10 ml) is added to a stirred suspension of phenylthioacetic acid (1.44 g) and 2-(O-hydroxyphenoxy)methyl-thiazolidine in dimethylformamide (15 ml).

After two hours, the dicyclohexylurea is filtered out and the solution is diluted with water (150 ml) and extracted with ethylether. The organic phases are collected and, after the usual work-up, the residual oil is purified by chromatography on $SiO_2$ (hexane-AcOEt 1:1) to give 1.8 g of 3-(phenylthioacetyl)-2-(hydroxyphenoxy)methylthiazolidine m.p. 94°–96° C.

In similar way, the following derivatives are prepared:
3-(phenylthioacetyl)-2-(O-methxyphenoxy)methyl-thiazolidine, m.p. 97°–99° C.;
3-(3-thia-pentanoyl)-2-(O-methoxypheoxy)methyl-thiazolidine, m.p. 66°–67° C.

EXAMPLE 51

A solution of 1-acetylcysteine disodium salt (638 mg) in MeOH (3 ml) is treated with a solution of 3-(α-chloroacetyl)-2-(O-methoxyphenoxy)methyl-thiazolidine (0.88 g) in dimethoxyethane (10 ml). After 2 hours at room temperature the mixture is evaporated to dryness and the residue is partitioned between ethyl acetate and aqueous 20% $NaH_2PO_4$ solution.

The organic phase, after the usual work-up, gives 0.76 g of 3-(5-carboxy-5-acetylamino-3-thia-pentanoyl)-2-(O-methoxyphenoxy)methyl-thiazolidine, m.p. 69°–78° C.

EXAMPLE 52

α-Methoxy-acetylchloride (7.3 ml) is added to a stirred solution of 14.8 g of 2-(O-methoxyphenoxy)methylthiazolidine and triethylamine (11.2 ml) in sym-dichloroethane (100 ml), cooled at 0°–5° C. After 1 hour, the mixture is washed with water. After the usual work-up and crystallization from isopropanol, 11.46 g of 3-(α-methoxyacetyl)-2-(O-methoxyphenoxy)methyl-thiazolidine, m.p. 76°–77° C., are obtained.

Using in the same procedure the 3,6-dioxa-capriloyl-chloride and the 3-thia-6-oxacapriloyl chloride, the following compounds are obtained:
3-(3,6-dioxa-capriloyl)-2-(O-methoxyphenoxy)methyl-thiazolidine, oil, H-NMR (CDCl$_3$-THMS): 1.3 (3H, t, CH$_2$—CH$_3$); 3.7 (6H, m, —O—CH$_2$—CH$_2$—O—CH$_2$); 3.8 (3H, s, O—CH$_3$); 6.5 (4H, s
3-(3-thia-6-oxa-capriloyl)-2-(O-methoxyphenoxy)methylthiazolidine, oil, H-NMR (CDCl$_3$-THMS): 1.3 (3H, t, CH$_2$CH$_3$); 3.82 (3H, s, OCH$_3$).

EXAMPLE 53

N,N'-Dicyclohexylcarbodiimide (22.7 g) is added to a stirred solution of 2-(O-methoxyphenoxy)methyl-thiazolidine (22.6 g), N-acetylglycine (12.9 g) and 4-dimethylaminopyridine (1.08 g) in a sym-dichloroethane cooled at 0° C. After 12 hours, the dicyclohexylurea is removed by filtration, and the organic phase is washed with 5% aqueous NaHCO$_3$, water and then it is dried on Na$_2$SO$_4$. After removal of solvents in vacuum, the residual oil is crystallized from isopropanol to give 3-(N-acetylaminoacetyl)-2-(O-methoxyphenoxy)methyl-thiazolidine, m.p. 119°–120° C. Using in this procedure BOC-glycine and N-formylglycine, the corresponding 3-(N-formylaminoacetyl)-2-(O-methoxyphenoxy)methyl-thiazolidine, m.p. 104°–106° C., 3-(BOC-glycinyl)-2-(O-methoxyphenoxy)methyl-thiazolidine oil, are prepared.

By treatment of the BOC-derivate with trifluoroacetic acid and methylene chloride at room temperature, using the procedure of the Example 2, and 3-(glycinyl) compound is prepared.

By treatment of a solution of the N-formyl-glycinyl compound (15.07 g) in methanol (250 ml) with 8N HCl solution in isopropanol (9 ml) for 8 hours at room temperature, followed by concentration of the mixture at volume of 50 ml and filtration, 12 g of 3-glycinyl-2-(O-methoxyphenoxy)methyl-thiazolidine. HCl m.p. 182°–184° C., are obtained.

EXAMPLE 54

A stirred solution of 3,5-dibromo-salicylaldehyde (8.37 g), 3-glycinyl-2-(O-methoxyphenoxy)methyl-thiazolidine-hydrochloride (9.54 g) and triethylamine (4.14 ml) in methanol (250 ml) is heated at reflux temperature for 3 hours and then cooled to room temperature. Stirring in continued for 8 hours to precipitate 15.12 g of 3-(2-(3,5-dibromo-2-hydroxy-benzylidenamino-acetyl)-2-(O-methoxyphenoxy)methyl-thiazolidine, m.p. 126°–130° C.

10% NaBH$_4$ on alumina (11.8 g) is added to a stirred solution of this compound in ethylacetate (250 ml). After 6 hours, the organic phase is filtered, washed with water and dried on Na$_2$SO$_4$.

After treatment with 8N HCl in isopropanol (4.8 ml), 3-(3',5'-dibromo-6'-hydroxyphenyl)methylaminoacetyl-2-(O-methoxyphenoxy)methyl-thiazolidine-hydrochloride (12.9 g), m.p. 193°–196° C., is obtained.

The following examples illustrate various unit dosage compositions containing a compound of the present invention as the active ingredient.

In case of diabetic patients, sorbitol can be used instead of saccharose.

EXAMPLE 55

| | | |
|---|---|---|
| 3-Acetylthioacetyl-2-(o-methoxyphenoxy)- | g | 0.50 |

| -continued | | |
|---|---|---|
| methyl-thiazolidine | | |
| Polysorbitan monooleate | g | 0.05 |
| Sodium carboxymethylcellulose | g | 0.30 |
| Mycrocrystalline cellulose | g | 0.70 |
| Citric acid | g | 0.1 |
| Sodium citrate | g | 0.8 |
| Sodium benzoate | g | 0.12 |
| Methyl p-hydroxybenzoate | g | 0.035 |
| Propyl p-hydroxybenzoate | g | 0.015 |
| Aroma | q.s. | |
| Sorbitol 70% | g | 20 |
| Saccharose | g | 30 |
| Water to | ml | 100. |

EXAMPLE 56

| | | |
|---|---|---|
| 3-(3,4,5-Trimethoxy)benzoylthioacetyl-2-(o-methoxyphenoxy)methyl-thiazolidine | g | 2.5 |
| Polyethylenglycol | g | 45 |
| Ethanol 95 to | ml | 100. |

EXAMPLE 57

| | | |
|---|---|---|
| 3-(4'-Methylpyperazin-1-yl)acetyl-2-(o-methoxyphenoxy)methyl-thiazolidine dihydrochloride | g | 0.61 |
| Saccharose | g | 50 |
| Sodium benzoate | g | 0.12 |
| Methyl-p-hydroxybenzoate | g | 0.035 |
| Propyl-p-hydroxybenzoate | g | 0.015 |
| Aroma | q.s. | |
| Water to | ml | 100. |

EXAMPLE 58

| | | |
|---|---|---|
| 3α-Acetylthioacetyl-2-(o-methoxyphenylthio)-methyl-4-carboxy-thiazolidine tromethamine salt | g | 0.653 |
| Saccharose | g | 50 |
| Sodium benzoate | g | 0.12 |
| Methyl-p-hydroxybenzoate | g | 0.035 |
| Propyl-p-hydroxybenzoate | g | 0.015 |
| Tromethamine | g | 0.303 |
| HCl | g | 0.053 |
| Aroma | q.b. | |
| Water to | ml | 100. |

EXAMPLE 59

Using cysteine hydrochloride instead of cysteamine in the procedure of the Examples 4 and 7, the following compounds are obtained:
4-carboxy-2-[2'-(o-hydroxyphenyl)ethyl]-thiazolidine, m.p. 182°–183° C.;
4-carboxy-2-[(o-hydroxyphenoxy)methyl]-thiazolidine, m.p. 182°–183° C.

We claim:
1. Compound of formula I

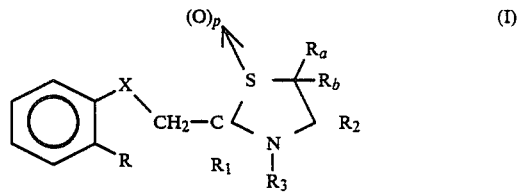

wherein:

X is a $CH_2$, O, S;
R is hydroxy, or an ester thereof of formula $R_c$—$CO_2$—, lower $C_1$-$C_6$-alkoxy, $CH_2$=CH—$CH_2O$—; HC≡C—$CH_2$—O—; methyl
$R_1$ is hydrogen or

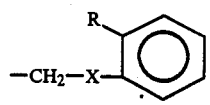

p is zero or 1 with the proviso that when X is sulfur p is zero;
both $R_a$ and $R_b$, are hydrogen or methyl;
$R_2$ is hydrogen and $R_3$ is, a $C_1$-$C_2$ alkylsulphonyl group, an unsubstituted or mono or polysubstituted phenylsulfonyl group or an acyl group of formula $R_dCO$—;
Rc and Rd, which are the same or different are: hydrogen, —O—$C(CH_3)_3$, —$(CH_2)_n$—Q and

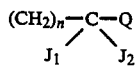

wherein n is 0 or an integer from 1 to 7;
$J_1$, $J_2$, are both hydrogen or one of them is hydrogen and the other one is lower $C_1$-$C_4$ alkyl or phenyl and Q is selected from the group consisting of:
hydrogen; a $C_3$-$C_4$-branched alkyl; a $C_3$-$C_7$ cycloalkyl; free or esterified carboxy group; an halogen atom; SH; —$NH_2$; a mono or di-substituted amino, t-butoxy carbonylamino or $C_1$-$C_2$ acylamino group; an ether —O—$(CH_2)_m$—T or thioether —S—T chain, wherein T is an unsubstituted or mono- or polysubstituted phenyl ring or a group of formula —$(CH_2)_m$—$T_1$, wherein $T_1$ is selected from the group consisting of H, OH, —$OCH_3$, $OC_2H_5$, $HOCH_2$—$CH_2$—, free and esterified carboxy group, $NH_2$, a $C_1$-$C_2$-acylamino or mono- or disubstituted amino group, or a group of formula

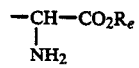

wherein $R_e$ is hydrogen, methyl or ethyl and m is an integer from 1 to 3; a phenyl, phenoxy or phenylthio ring unsubstituted or mono- or polysubstituted in the m, o, and p-positions;
a group of formula —$(CH_2)_m$—SCO—$(CH_2)_nJ$ wherein m and n have the above defined meanings and $P_3$ is a lower $C_1$-$C_7$ linear or branched alkyl chain, a $C_3$-$C_6$-cycloalkyl, a disubstituted amino group, a phenyl or phenoxy ring, optionally mono- or polysubstituted in the o, m and p-positions; an alkenyl chain of formula

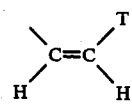

wherein T, in addition to the above defined meanings, is also hydrogen; or $R_2$ is a free or esterified carboxy group; and
$R_3$ is hydrogen, a $C_1$-$C_2$ alkylsulphonyl group, an unsubstituted or mono or polysubstituted phenylsulfonyl group or an acyl group of formula $R'_dCO$';
wherein R'd is hydrogen, —O—$C(CH_3)_3$, —$(CH_2)_n$—Q' and

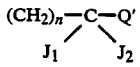

wherein n is 0 or an integer from 1 to 7; $J_1$, $J_2$, are both hydrogen or one of them is hydrogen and the other one is lower $C_1$-$C_4$ alkyl or phenyl and Q' is selected from the group consisting of:
hydrogen; a $C_3$-$C_4$-branched alkyl; a $C_3$-$C_7$ cycloalkyl; free or esterified carboxy group; —$NH_2$; a mono or disubstituted amino, t-butoxy carbonylamino or $C_1$-$C_2$ acylamino group; an ether —O—$(CH_2)_m$—T or thioether —S—T chain, wherein T is an unsubstituted or mono- or polysubstituted phenyl ring or a group of formula $(CH_2)_m$—$T_1$, wherein $T_1$ is selected from the group consisting of H, OH, $OCH_3$, —$OC_2H_5$, $HOCH_2$—$CH_2$—, free and esterified carboxy group, $NH_2$, a $C_1$-$C_2$-acylamino or mono- or disubstituted amino group, or a group of formula

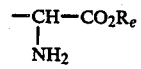

wherein $R_e$ is hydrogen, methyl or ethyl and m is an integer from 1 to 3; a phenyl, phenoxy or phenylthio ring unsubstituted or mono- or polysubstituted in the m, o, and p-positions;
wherein the term "mono substituted amino group" means an amino group substituted by a $C_1$-$C_6$ linear or branched alkyl group or by groups having the formula:

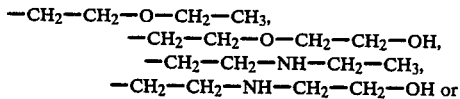

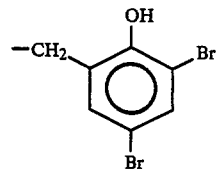

wherein the substituents of a disubstituted amino group are linear or branched $C_1$-$C_6$ alkyl groups or:
and wherein the term "mono- or polysubstituted phenyl" means phenyl which is substituted by a fluorine atom in the para position, by chlorine atoms in the meta and/or para positions, or by a $CF_3$ group in the meta position, or a phenyl group of the formula:

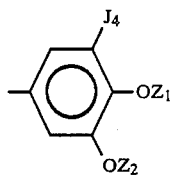

wherein Z₁ is H or COCH₃ and Z₂ is H, CH₃ or COCH₃ and J₄ is hydrogen, aminomethyl, C₁-C₂-acylaminomethyl or a mono or disubstituted aminomethyl group, as above defined; or salts with non-toxic bases or acids thereof, enantiomers, diastereoisomers or mixtures thereof.

2. A compound according to claim 1, wherein R₁ is hydrogen and p is zero.

3. A compound according to claim 1, wherein R₁, R_a and R_b are hydrogen, p is zero, X is an oxygen atom and R₃ is a group of formula R_dCO wherein R_d has the above defined meanings.

4. Compound of formula I:

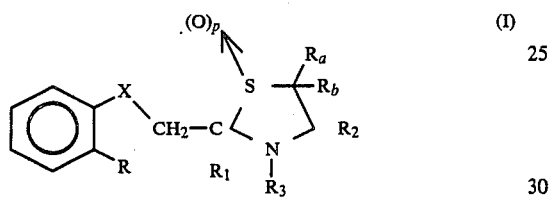

wherein:

X is a CH₂, O, S;

R is hydroxy, or an ester thereof of formula R_c—CO₂—; lower C₁-C₆-alkoxy; CH₂=CH—CH₂O—; HC≡C—CH₂—O—; or methyl R₁ is hydrogen or

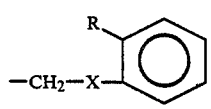

R₂ is hydrogen;

R₃ is hydrogen, a C₁-C₂ alkylsulphonyl group, an unsubstituted or mono or polysubstituted phenylsulfonyl group or an acyl group of the formula R_dCO—;

p is zero or 1 with the proviso that when X is sulfur p is zero;

both R_a and R_b, are hydrogen or methyl; Rc and Rd, which are the same or different are:
hydrogen, —O—C(CH₃)₃, —(CH₂)ₙ—Q and

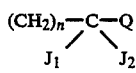

wherein n is 0 or an integer from 1 to 7; J₁, J₂ are both hydroben or one of them is hydrogen and the other one is lower C₁-C₄ alkyl or phenyl; and Q is selected from the group consisting of:
hydrogen; a C₃-C₄-branched alkyl; a C₃-C₇ cycloalkyl; free or esterified carboxy group; an halogen atom; SH; —NH₂; a mono or disubstituted amino, t-butoxy carbonylamino or C₁-C₂ acylamino group; an ether —O—(CH₂)ₘ—T or thioether —S—T chain, wherein T is an unsubstituted or mono- or polysubstituted phenyl ring or a group of formula —(CH₂)ₘ—T₁, wherein T₁ is selected from the group consisting of H, OH, OCH₃, —OC₂H₅, —OCH₂—CH₂—, free and esterified carboxy group, NH₂, a C₁-CH₂-acylamino or mono- or disubstituted amino group, or a group of formula

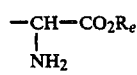

wherein R_e is hydrogen, methyl or ethyl and m is an integer from 1 to 3; a phenyl, phenoxy or phenylthio ring unsubstituted or mono- or polysubstituted in the m, o, and p-positions;
a group of formula —(CH₂)ₘ—SCO—(CH₂)ₙJ₃ wherein m and n have the above defined meanings and J₃ is a lower C₁-C₇ linear or branched alkyl chain, a C₃-C₆-cycloalkyl, a disubstituted amino group, a phenyl or phenoxy ring, optionally mono- or polysubstitued in the o, m and p-positions; an alkenyl chain of formula:

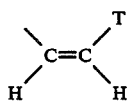

wherein T, in addition to the above defined meanings, is also hydrogen;

wherein the term "mono substituted amino group" means an amino group substituted by a C₁-C₆, linear or branched alkyl group or by groups having the formula:

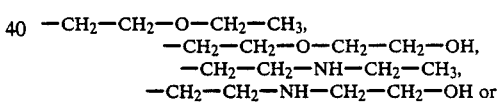

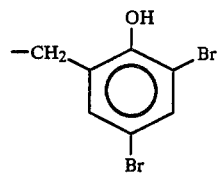

wherein the substituents of a disubstituted amino group are linear or branched C₁-C₆ alkyl group or:
and wherein "mono- or polysubstituted phenyl", means phenyl which is substituted by a fluorine atom in the para position, by chlorine atoms in the meta and/or para positions, or by a CF₃ group in the meta position, or a phenyl group of the formula:

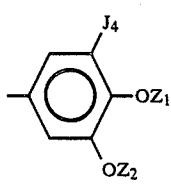

wherein $Z_1$ is H or —COOH$_3$ and $Z_2$ is H, CH$_3$ or —COCH$_3$ and $J_4$ is hydrogen, aminomethyl, C$_1$-C$_2$-acylaminomethyl or a mono- or disubstituted aminomethyl group, as above defined; or salts with non-toxic bases or acids thereof, enantiomers, diastereoisomers or mixtures thereof.

5. Compound of formula I

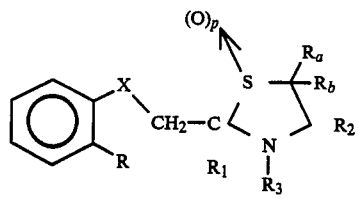

wherein:

X is a CH$_2$, O, S;

R is hydroxy, or an ester thereof of formula R$_c$—CO$_2$—, lower C$_1$-C$_6$-alkoxy, CH$_2$=CH—CH$_2$O—; HC≡C—CH$_2$—O—; methyl R$_1$ is hydrogen or

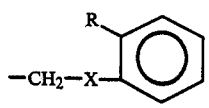

p is zero or 1 with the proviso that when X is sulfur p is zero;

both R$_a$ and R$_b$, are hydrogen or methyl;

R$_2$ is hydrogen or a free or esterified carboxy

R$_3$ is a C$_1$-C$_2$ alkylsulphonyl group, an unsubstituted or mono or polysubstituted phenylsulfonyl group or an acyl group of formula R$_d$CO—;

Rc and Rd, which are the same or different are: hydrogen, —O—C(CH$_3$)$_3$, —(CH$_2$)$_n$—Q and

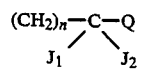

wherein n is 0 or an integer from 1 to 7;

J$_1$, J$_2$, are both hydrogen or one of them is hydrogen and the other one is lower C$_1$-C$_4$ alkyl or phenyl; and Q is selected from the group consisting of hydrogen; a C$_3$-C$_4$-branched alkyl; a C$_3$-C$_7$ cycloalkyl; free or esterified carboxy group; —NH$_2$; a mono or di-substituted amino, t-butoxy carbonylamino or C$_1$-C$_2$ acylamino group; an ether —O—(CH$_2$)$_m$—T or thioether —S—T chain, wherein T is an unsubstituted or mono- or polysubstituted phenyl ring or a group of formula (CH$_2$)$_m$—T$_1$, wherein T$_1$ is selected from the group consisting of H, OH, OCH$_3$, —OC$_2$H$_5$, HOCH$_2$—CH$_2$—, free and esterified carboxy group, NH$_2$, a C$_1$-C$_2$-acylaminor or mono- or disubstituted amino group, or a group of formula

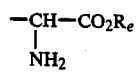

wherein R$_e$ is hydrogen, methyl or ethyl and m is an integer from 1 to 3; a phenyl, phenoxy or phenylthio ring unsubstituted or mono- or polysubstituted in the m, o, and p-positions;

wherein the term "mono substituted amino group" means an amino group substituted by a C$_1$-C$_6$, linear or branched alkyl group or by groups having the formula:

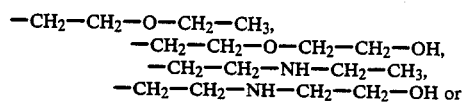

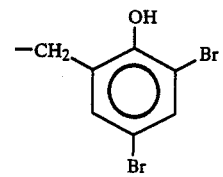

wherein the substituents of a disubstituted amino group are linear or branched C$_1$-C$_6$ alkyl groups or:

and wherein the term "mono- or polysubstituted phenyl" means phenyl which is substituted by a fluorine atom in the para position, by chlorine atoms in the meta and/or para positions, or by a CF$_3$ group in the meta position, or a phenyl group of the formula:

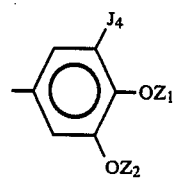

wherein $Z_1$ is H or COCH$_3$ and $Z_2$ is H, CH$_3$ or COCH$_3$ and $J_4$ is hydrogen, aminomethyl, C$_1$-C$_2$-acylaminomethyl or a mono or disubstituted aminomethyl group, as above defined; or salts with non-toxic bases or acids thereof, enantiomers, diastereoisomers or mixtures thereof.

6. Compound of claim 1, wherein R$_1$, R$_2$, R$_a$ and R$_b$ are each hydrogen, X is O, R is methoxy, p is 0, R$_3$ is R$_d$CO— wherein R$_d$ is —(CH$_2$)$_n$—Q and Q is esterified carboxy, disubstituted amino, or —(CH$_2$)$_m$—S—CO—(CH$_2$)$_n$J$_3$.

7. Compound of claim 6, wherein Q is esterified carboxy.

8. A compound selected from the group consisting of:

2-(O-methoxyphenoxy)methyl-3-acetylthioacetyl-thiazolidine;

2-(O-methoxyphenoxy)methyl-3-benzoylthioacetyl-thiazolidine;

2-(O-methoxyphenoxy)methyl-3-(3',4',5'-trimethoxy)-benzoylthioacetyl-thiazolidine;

2-(O-methoxyphenoxy)methyl-3-(4'-methyl-pyrazin-1-yl-;

2-(O-methoxyphenoxy)methyl-3-cyclopropylcarbonyl-thioacetyl-thiazolidine;

2-(O-methoxyphenoxy)methyl-3-(3'-cyclohexyl)propionylthioacetyl-thiazolidine;

2-(O-methoxyphenoxy)methyl-3-acetylthioacetyl-thiazolidine-sulfoxide;

2-(O-hydroxyphenoxy)methyl-3-ethoxyoxalyl-thiazolidine and its methylether;

2-(O-hydroxyphenoxy)methyl-3-cyclopropylcarbonyl-thiazolidine and its methylester;
2-(O-acetylthioacetoxy-phenoxy)methyl-3-acetylthioacetyl-thiazolidine;
2-[2'-(O-acetylthioacetoxyphenyl)ethyl]-3-acetylthioacetyl-thiazolidine;
2-(O-methoxyphenylthio)methyl-3-benzoylthioacetyl-thiazolidine;
2-[2'-(O-methoxyphenyl)ethyl]-3-benzoylthioacetyl-thiazolidine;
3-[3-(2-hydroxyethylamino)ethylaminopropanoyl]-2-(O-methoxyphenoxy)methyl-thiazolidine and its maleate;
3-(acetylaminoacetyl)-2-(O-methoxyphenoxy)methyl-thiazolidine.

9. Pharmaceutical compositions having mucus regulating, bronchodilatory and/or antitussive activity containing a therapeutically effective amount of a compound as claimed in any one of claims 1, 4 or 5 in admixture with non-toxic carriers or excipients.

10. 2-(O-methoxy phenoxy)methyl-3-acetylthioacetylthiazolidine or a salt thereof with a non-toxic base or acid, an enantiomer, a diastereisomer, or a mixture thereof.

11. Compound of claim 1, wherein $R_3$ is $-CO-(CH)_n-(CH_2)_m-SCO-(CH_2)_n-P_3$.

12. Compound of claim 1, wherein $R_3$ is $-CO-CH_2-S-CO-CH_3$.

13. Compound of claim 1, wherein X is O or S.

14. Compound of claim 1, wherein X is O.

15. Compound of claim 1, wherein R is hydroxy or an ester thereof of formula $R_c-CO_2-$; lower $C_1$-$C_6$ alkoxy, $CH_2=CH-CH_2O-$; or $HC\equiv C-CH_2-O-$.

* * * * *